(12) United States Patent
Nishino et al.

(10) Patent No.: US 6,399,568 B1
(45) Date of Patent: Jun. 4, 2002

(54) CYCLIC TETRAPEPTIDE DERIVATIVES AND MEDICINAL USE THEREOF

(75) Inventors: Norikazu Nishino, Fukuoka; Minoru Yoshida, Saitama; Sueharu Horinouchi, Tokyo; Yasuhiko Komatsu; Tsutomu Mimoto, both of Saitama, all of (JP)

(73) Assignee: Japan Energy Corporation, Tokyo (JP)

( * ) Notice: Subject to any disclaimer, the term of this patent is extended or adjusted under 35 U.S.C. 154(b) by 0 days.

(21) Appl. No.: 09/486,783

(22) PCT Filed: Sep. 1, 1998

(86) PCT No.: PCT/JP98/03893

§ 371 (c)(1),
(2), (4) Date: Mar. 1, 2000

(87) PCT Pub. No.: WO99/11659

PCT Pub. Date: Mar. 11, 1999

(30) Foreign Application Priority Data

Sep. 2, 1997 (JP) .............................. 9-237481
Mar. 13, 1998 (JP) .............................. 10-63270

(51) Int. Cl.[7] .......................... A61K 38/12; C07K 5/12
(52) U.S. Cl. ........................................ 514/11; 530/321
(58) Field of Search .................... 514/9.11; 530/317, 530/321

(56) References Cited

PUBLICATIONS

Kijima et al. Trapoxin, an Antitumor Cyclic Tetrepeptide . . . J. Bid Chem. vol. 268, No. 30, pp. 22429–22435, Oct. 25, 1993.

(List continued on next page.)

Primary Examiner—Jeffrey E. Russel

(74) Attorney, Agent, or Firm—Fish & Richardson P.C.

(57) ABSTRACT

A cyclic tetrapeptide derivative represented by the general formula (I):

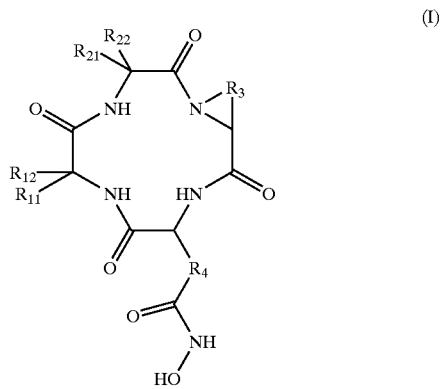

wherein:

$R_{11}$, $R_{12}$, $R_{21}$ and $R_{22}$ independently denote a monovalent group selected from hydrogen, a linear or branched alkyl group with 6 or less carbon atoms, benzyl group, 4-methoxybenzyl group, 3-indolylmethyl group, (N-methoxy-3-indolyl) methyl group, (N-formyl-3-indolyl)methyl group, etc.; $R_3$ denotes a divalent group selected from a linear chained hydrocarbon group with 3 or 4 carbon atoms, or the linear branched hydrocarbon group having a branched chain added to the chain, or a divalent group substituted with a heteroatom;

$R_4$ denotes a divalent chained hydrocarbon group with 4 to 6 carbon atoms, or a divalent group derived from said hydrocarbon group by addition etc. of a branched chain on said chain; and a pharmaceutically acceptable salt thereof, or an analogous cyclic tetrapeptide derivative compound; as well as a histone deacetylase enzyme inhibitor, an MHC class-I molecule expression promoting agent and a pharmaceutical composition that comprise said cyclic tetrapeptide derivative as an effective ingredient.

9 Claims, 7 Drawing Sheets

OTHER PUBLICATIONS

Bernardi et al. Antitumoral Cyclic Peptide Analogues . . . Peptides. vol. 14, pp. 1091–1093, 1993.

Bernardi et al. Synthesis of New Cytotxic Cyclopeptide Anologs . . . Bull. Soc. Chim. Fr. vol. 131, pp. 944–948, 1994.

Acetylated lysine

Trapoxin A

Trapoxin B

Cyl-2

WF-3161

Chlamydocin

HC-toxin

```
                       SEQUENCE LISTING

<160> NUMBER OF SEQ ID NOS: 1

<210> SEQ ID NO 1
<211> LENGTH: 22
<212> TYPE: PRT
<213> ORGANISM: Artificial Sequence
<220> FEATURE:
<223> OTHER INFORMATION: synthetically generated p eptide

<400> SEQUENCE: 1

Ser Gly Arg Gly Lys Gly Gly Lys Gly Leu G ly Lys Gly Gly Ala Lys
 1               5                  10                  15

Arg His Arg Lys Val Cys
             20
```

CYCLIC TETRAPEPTIDE DERIVATIVES AND MEDICINAL USE THEREOF

TECHNICAL FIELD

The present invention relates to novel cyclic tetrapeptide derivatives or pharmaceutically acceptable salts thereof, application of said compounds as histone deacetylase inhibitors and MHC class-I molecule expression promoting agents, as well as pharmaceutical compositions that comprise said cyclic tetrapeptide derivatives or pharmaceutically acceptable salts thereof as effective ingredients and which have utility as pharmaceuticals such as anti-cancer agents by taking advantage of the aforementioned histone deacetylase inhibiting or MHC class-I molecule expression promoting action.

BACKGROUND ARTS

Tissue cells of a self inherently express on their cell surface an MHC class-I molecule as an antigen presenting molecule to discriminate externally invading foreign matters and pathogens from themselves and prevent false damage by their immunocytes. The immune system, looking at the MHC class-I molecule, identifies the tissue cells of a self and eliminates them from the target of its attack. On the other hand, cancerized cells or cells infected with cancer viruses, which are originally cells of a self, differ from normal cells of a self in that they produce proteins associated with cancer or proteins derived from the cancer viruses, and antigens derived from these non-self proteins are presented by the MHC class-I molecule. The immunocytes, in particular cytotoxic T cells, can recognize the non-self protein-derived antigens, thereby excluding the cancer cells or cancer virus-infected cells.

It has been reported, however, that in certain kinds of cancer cells or cancer virus infected cells, the expression of the MHC class-I molecule is reduced, so that the aforementioned exclusion mechanism by the immune system is circumvented, causing expansion and enlargement of cancerized tissues as well as prolonged sustention and enlargement of cancer virus infection. In the studies for the purpose of preventing tumorization of the cancerized cells or cancer virus infected cells, some results have been reported suggesting that therapeutic effects may be attained by recovery of the reduced expression of the MHC class-I molecule. For example, Tanaka et al. reported that in cancer cells transformed with adenovirus 12 or spontaneous melanoma, tumorization of these cancer cells may disappear upon enhancing the reduced expression of the MHC class-I molecule through introduction of MHC class-I gene: see Tanaka, R., Isselbacher, K. J., Khoury, G. and Jay, G., Science, 228, 26–30, 1985; Tanaka, K., Gorelik, E., Watanabe, M., Hozumi, N. and Jay, G., Mol. Cell. Biol., 8, 1857–1861, 1988.

By the way, the expression of MHC class-I molecule occurs during the differentiation processes after the growth of the self tissue cells, and the expression of MHC class-I molecule is expected to be promoted by promoting the translation of endogenous proteins in this process. While there are several mechanisms which control the translation of endogenous proteins, one of those which may be considered to play an important role in gene expression is acetylation of histone proteins contained in the nuclear gene chromatins as their structural proteins. Illustratively, chromatin is composed of the basic unit referred to as a nucleosome structure, in which a gene DNA is wound around four core histone octamers. Further, the basic units form higher-order structure. The neighborhood of the N-terminal of the core histone is in the form of a tail rich in basic amino acids and it further encloses the DNA on the aforementioned nucleosome. Lysine residues in the neighborhood of the tail region undergo reversible metabolic turnover of acetylation and are said to be closely involved in the structural control of nucleosome itself or in the transcriptional control through the control of binding with other proteins acting on gene DNA, such as transcriptional factors, silencer proteins and RNA polymerase.

As a demonstration of gene expression control depending on acetylation of histone, it has been reported that higher acetylation of histone promotes the induced expression from genes present in a region of interest while deacetylation forms a transcriptional inactive region called heterochromatin. That is to say, histone which is a structural protein of chromatin and its acetylation are extended over the whole region of the chromosomal gene; nevertheless, it has been suggested that the function of histone greatly affects the expression of a specific gene and, in other words, is involved in the strict control of nuclear signal transmission. An enzyme for acetylating histone is histone acetyl transferase while an enzyme for deacetylating histone is histone deacetylase; these enzymes regulate the kinetic metabolic turnover relating to the level of histone acetylation.

If the action of histone deacetylase is accentuated, proper differentiation of cells or normalization of their morphology is inhibited: however, when the enzyme activity of the histone deacetylase is inhibited, the deacetylation from histone is inhibited and, as a result, high acetylation of histone is caused to induce the gene expression required for differentiation and normalization of cell morphology. This phenomenon has been confirmed to some extent by studies using trichostatin A shown in FIG. 1 or trapoxin analogs shown in FIG. 2, which are enzyme inhibitors of histone deacetylase. In addition, when these inhibitors are allowed to act on cells at higher concentrations, cell cycle inhibition is caused and consequently growth inhibition occurs. Trichostatin A exhibits a non-competitive enzyme inhibiting actions at low concentrations and is a reversible inhibitor; on the other hand, trapoxin analogs exhibit competitive inhibitory actions but are irreversible inhibitors. Further, it has also been reported that enzymatically active subunits of human derived histone deacetylase were purified on an affinity column using K-trap that is a cyclic tetrapeptide compound similar to trapoxin; thus, strong evidence has been given to demonstrate that the cyclic tetrapeptide structure as found in trapoxin and the like forms a selective intermolecular linkage with said enzymatically active subunit.

As stated above, since an enzyme inhibitory substance of histone deacetylase is a drug causing cell differentiation or normal morphogenesis, it may also exhibit a promoting action in the expression of MHC class I molecule which occurs as a step in the process of differentiation; however, no report confirming Gis possibility has been made to date.

Accordingly, there is a strong need for search and proposal of histone deacetylase enzyme inhibitory substances that exhibit promoting actions on the expression of MHC class-I molecule in self tissue cells. Further, as stated above, a histone deacetylase enzyme inhibiting substance at a high concentration causes the inhibition of cell cycle and consequently exhibits growth inhibiting action so a need exists for the proposal of a novel anti-cancer agent that is based on the promotion of the MHC class-I molecule expression and which exhibits a combined anti-cancer action due to the contributions of not only the inhibition of tumorization and the exclusion of cancer cells by immune system, but also the cell growth inhibiting action, all being associated with the promotion of MHC class-I molecule expression.

The present invention solves the aforementioned problems and an object of the present invention is to provide a histone deacetylase enzyme inhibiting substance exhibiting a promoting action on the expression of MHC class-I molecule in self tissue cells and to provide a pharmaceutical composition comprising said histone deacetylase enzyme inhibiting substance as an effective ingredient.

DISCLOSURE OF THE INVENTION

To solve the aforementioned problems, the present inventors have eagerly studied and found that trichostatin A or its analogous compound trichostatin C that have a histone deacetylase enzyme inhibiting activity promotes the expression of MHC class-I molecule when they were allowed to act on animal cells and further found that in addition to the said trichostatins, butyric acid and trapoxin A that have the histone deacetylase enzyme inhibiting activity also exhibit the MHC class-I molecule expression promoting activity. Based on these findings, various cyclic tetrapeptide derivatives have been created and these cyclic tetrapeptide derivatives have been found to inhibit the enzyme activity of histone deacetylase reversibly and exhibit the MHC class-I molecule expression promoting activity. Thus, the present invention has been completed.

Accordingly, the present invention relates to a cyclic tetrapeptide derivative represented by any one of the general formula (I):

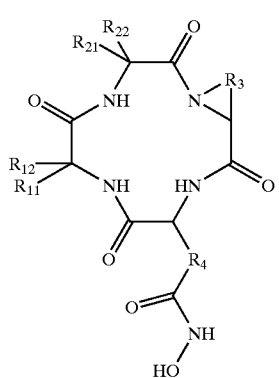

(I)

the general formula (I'):

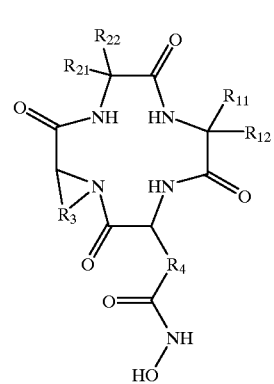

(I')

the general formula (I''):

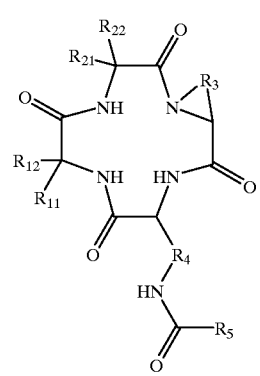

(I'')

and the general formula (I'''):

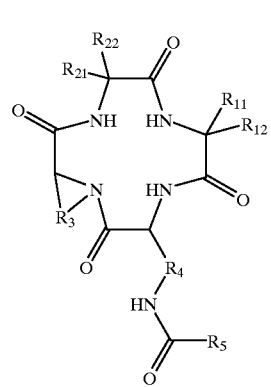

(I''')

wherein:
$R_{11}$, $R_{12}$, $R_{21}$ and $R_{22}$ independently denote a monovalent group selected from hydrogen, linear alkyl groups with 1 to 6 carbon atoms, branched alkyl groups with 3 to 6 carbon atoms, linear ω-aminoalkyl groups with 1 to 5 carbon atoms, branched aminoalkyl groups with 3 to 5 carbon atoms, N-acyl-aminoalkyl groups in which the amino group on said linear or branched aminoalkyl groups is substituted with an acyl group or a halogeno-substituted acyl group that have 3 or less carbon atoms, benzyl group, 4-methoxybenzyl group, 3-indolylmethyl group, (N-methoxy-3-indolyl)methyl group, (N-acyl-3-indolyl)methyl groups having an acyl group with 3 or less carbon atoms as a substituent on the ring-forming nitrogen atom, and methyl group substituted with an aryl group comprising 4 or less rings;

$R_3$ denotes a divalent group selected from linear alkylene groups with 3 or 4 carbon atoms in the chain which may have a branched chain on the chain, linear alkenyleno group with 3 or 4 carbon atoms in the chain which may have a branched chain on the chain, linear alkadienylene groups with 4 carbon atoms in the chain which may have a branched chain on the chain, and those divalent groups in which the branched chain added onto said linear alkylene, linear alkenylene or alkadienylene group form a fused ring structure, as well as those divalent groups in which among the carbon atoms constituting the chained hydrocarbon groups, one of the carbon atoms other than that having a free valence has been replaced with a heteroatom oxygen, sulfur or nitrogen;

$R_4$ denotes a divalent chained hydrocarbon group with 4 to 6 carbon atoms in the chain which may have a branched chain on said chain, or a divalent group in which among the carbon atoms constituting the chained hydrocarbon groups, at least one of the carbon atoms other than that having a free valence has been replaced with a heteroatom oxygen, sulfur or nitrogen;

$R_4$ denotes a divalent chained hydrocarbon group with 4 to 6 carbon atoms in the chain which may optionally have a branched chain on said chain, or a divalent group in which among the carbon atoms constituting the chained hydrocarbon groups, at least one of the carbon atoms other than that having a free valence has been replaced with a heteroatom oxygen, sulfur or nitrogen; and $R_5$ in the general formulae (I") or (I''') denotes a methyl group or halogeno-substituted methyl group, or a pharmaceutically acceptable salt thereof; a histone deacetylase inhibitor comprising said cyclic tetrapeptide derivative or pharmaceutically acceptable salt thereof; an MHC class-I molecule expression promoting agent comprising said cyclic tetrapeptide derivative or pharmaceutically acceptable salt thereof as an effective ingredient; as well as a pharmaceutical composition, such as an anti-cancer agent, comprising said cyclic tetrapeptide derivative or pharmaceutically acceptable salt thereof as an effective ingredient.

BEST MODE FOR CARRYING OUT THE INVENTION

Figure 1:
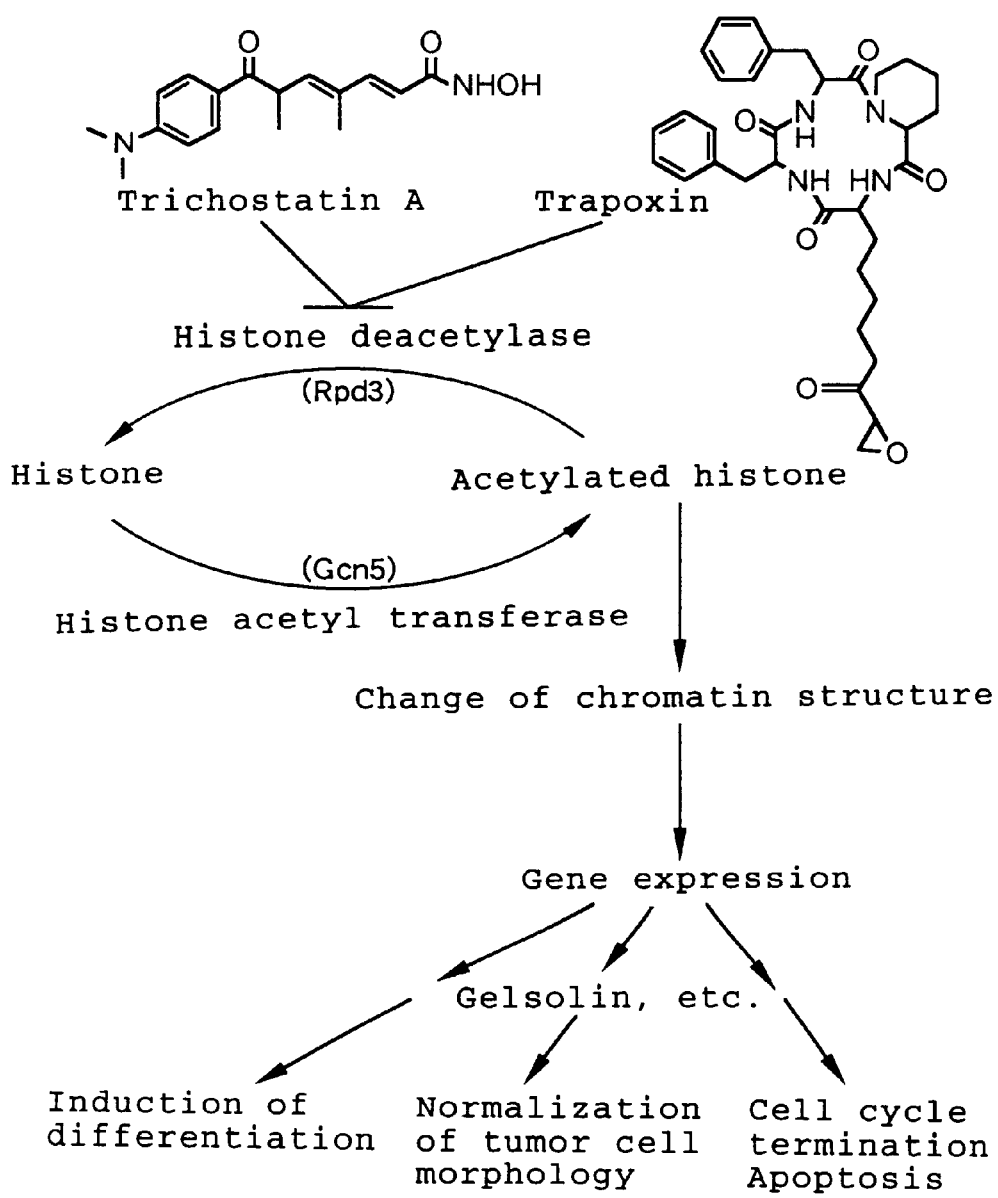
FIG. 1 shows the molecular structures of trichostatin A and trapoxin, as well as the action thereof to inhibit histone deacetylation.

The cyclic tetrapeptide derivatives of the present invention and processes for preparing them will be hereinafter described in more detail. In addition, the pharmacological activities of said cyclic tetrapeptide derivatives will be generally described.

As stated above, the cyclic tetrapeptide derivatives are represented by any one of the four mutually related structures shown by the general chemical formulae (I) to (I'''). First, it will be described that these four molecular structures have mutual close relationship to each other in their structures as stated below and that in this sense, they are compounds having a high degree of structural similarity.

The cyclic tetrapeptide derivative represented by the general formula (I) according to the present invention is obtained by first ligating the four constituent amino acids to prepare a corresponding chained tetrapeptide derivative and then cyclizing the chained tetrapeptide derivative. Thus, a cyclic tetrapeptide skeleton is formed through peptide linkages of the following four α-amino acids represented by the general formulae (II) to (V), i.e., an α-amino acid represented by the following general formula (II):

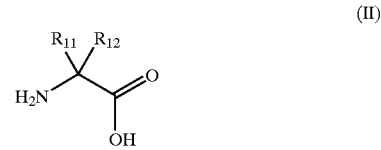

(II)

wherein $R_{11}$ and $R_{12}$ denote the same groups as $R_{11}$ and $R_{12}$ in the general formula (I), respectively; an α-amino acid represented by the general formula (III):

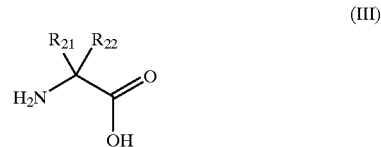

(III)

wherein $R_{21}$ and $R_{22}$ denote the same groups as $R_{21}$ and $R_{22}$ in the general formula (I), respectively; a cyclic α-amino acid represented by the general formula (IV):

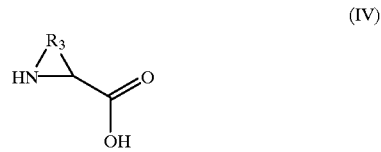

(IV)

wherein $R_3$ denotes the same group as $R_3$ in the general formula (I); and an α-amino acid represented by the general formula (V):

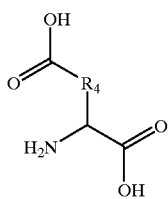
(V)

wherein $R_4$ denotes the same group as $R_4$ in the general formula (I), and then a hydroxamic acid is derived from the side chain carboxyl group in the aforementioned general formula (V).

The cyclic tetrapeptide derivatives represented by the general formula (I') correspond to the cyclic tetrapeptide derivatives represented by the aforementioned general formula (I), except that the formation of the peptide chain is performed in the reverse direction. Thus, the cyclic tetrapeptide derivatives represented by the general formula (I) have an amino acid sequence in which the four α-amino acids represented by the general formulae (II) to (V) are linked in the order of (II)–(III)–(IV)–(V) from the N-terminal to the C-terminal; on the other hand, the cyclic tetrapeptide derivatives represented by the general formula (I') have an amino acid sequence in which the four α-amino acids represented by the same general formulae (II) to (V) are linked in the order of (V)–(IV)–(III)–(II) from the N-terminal to the C-terminal.

The cyclic tetrapeptide derivatives represented by the general formula (I") according to the present invention is such that the α-amino acid having a carboxyl group on the side chain that is represented by the general formula (V) in the cyclic tetrapeptide derivatives represented by the general formula (I) is replaced with an α-amino acid having an amino group on the side chain that is represented by the following general formula (V'):

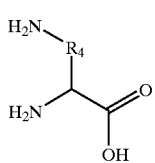
(V')

wherein $R_4$ denotes the same group as $R_4$ in the general formula (I"), and that the four α-amino acids represented by the general formulae (II) to (IV) and the general formula (V') are linked to each other in the same order, i.e., in the order of (II)–(III)–(IV)–(V') from the N-terminal to the C-terminal, through peptide linkage to form a cyclic tetrapeptide skeleton, followed by modifying the side chain amino group in the aforementioned general formula (V') with an acyl group.

The cyclic tetrapeptide derivatives represented by the general formula (I''') correspond to the cyclic tetrapeptide derivatives represented by the aforementioned general formula (I"), except that the formation of the peptide chain is performed in the reverse direction. Thus, the cyclic tetrapeptide derivatives represented by the general formula (I") have an amino acid sequence in which the four α-amino acids represented by the general formulae (II) to (V') are linked in the order of (II)–(III)–(IV)–(V') from the N-terminal to the C-terminal; on the other hand the cyclic tetrapeptide derivatives represented by the general formula (I''') have an amino acid sequence in which the four α-amino acids represented by the same general formulae (II) to (V') are linked in the order of (VI)–(IV)–(III)–(II) from the N-terminal to the C-terminal.

In the cyclic peptides represented by the general formula (I) of the present invention, the configuration of their constituent α-amino acids may be either L- or D-configuration; preferably, at least one amino acid residue has a different configuration than the other amino acid residues in order to ensure structural stability. Illustratively, at least one of the four α-amino acids advantageously has D-configuration while the remainder have L-configuration. For instance, if one D-configuration is to be selected from the four α-amino acids, the α-amino acid of either the general formula (II) or the general formula (IV) which is adjacent to the α-amino acid of the general formula (V) may take D-configuration. If two D-configurations are to be selected, both the α-amino acids of the general formula (II) and the general formula (IV) which are adjacent to the α-amino acid of the general formula (V) may take D-configuration. If both the a-amino acids of the general formula (II) and the general formula (III) are glycine, that is, $R_{11}$, $R_{12}$, $R_{21}$ and $R_{22}$ are all hydrogens, the remaining two amino acids may both take the same configuration. In this special case of selection, the presence of the contiguous two glycines permits the cyclic peptide, taken as a whole, to maintain its structural stability due to the high flexibility of this site.

More preferably, among the aforementioned four amino acids, D-configuration may be chosen for the cyclic amino acid represented by the general formula (IV), while the remaining three take L-configuration; or, L-configuration may be chosen for the amino acid represented by the general formula (IV) while the remaining three take D-configuration. Alternatively, among the aforementioned four amino acids, both the α-amino acid of the general formula (IV) which is a cyclic amino acid and the amino acid of the general formula (II) take more preferably D-configuration while the remaining two take L-configuration. In particular, when the side chain in the α-amino acid residue of the general formula (II) is bulky, both the α-amino acid of the general formula (IV) which is a cyclic amino acid and the α-amino acid of the general formula (II) take more preferably D-configuration while the remaining two take L-configuration. That is, in the cyclic peptide of interest, the site near the enzymatically active site of histone deacetylase is not the side chain of N-acetylated lysine which is an inherent substrate for the enzyme but hydroxamic acid derived from the side chain carboxyl group in the amino acid of the general formula (V), go it is more preferable to select L-configuration for the amino acid of the general formula (V) as in the case of naturally occurring lysine. Therefore, in still more preferable embodiments, D-configuration is selected for the cyclic amino acid represented by the general formula (IV) while the remaining three take L-configuration; or D-configuration is selected for both the α-amino acid of the general formula (IV) which is a cyclic amino acid and the α-amino acid of the general formula (II) while the remaining two take L-configuration.

More preferably, among the aforementioned four amino acids, D-configuration may be chosen for the cyclic amino acid represented by the general formula (IV), while the remaining three take L-configuration; or, L-configuration may be chosen for the amino acid represented by the general formula (IV) while the remaining three take D-configuration. It should also be noted that in the cyclic peptide of interest, the enzymatically active site of histone deacetylase is not the side chain of N-acetylated lysine which is an inherent substrate for the enzyme but hydroxamic acid derived from the side chain carboxyl group in the amino acid of the general formula (V), so it is more preferable to select L-configuration for the amino acid of the general formula (V) as in the case of naturally occurring lysine. Therefore, In still more preferable embodiments, D-configuration is selected for the cyclic amino acid represented by the general formula (IV) while the remaining three take L-configuration.

Now, the side chain hydroxamicacid structure: —$R_4$—CO—NH—OH derived from the amino acid side chain of the general formula (V) will be described. As stated above, this site is substituted for the side chain of N-acetylated lysine: —$(CH_2)_4$—NH—CO—$CH_3$ which is an inherent substrate for the enzyme of interest and the length of the chain of the divalent group $R_4$ is preferably at least 4 but not more than 6. If the chain length of $R_4$ is less than 4, Suitable access to the enzymatically active site of histone deacetylase can not be realized. On the other hand, $R_4$ having a chain length of 7 or more is unduly long. In any of these cases, the ability to inhibit the enzymatic activity of histone deacetylase will be significantly damaged.

The divalent group $R_4$ may be unbranched like the side chain of N-acetylated lysine or it may have a branched chain on the chain like the corresponding chain portion of a known inhibitor trichostatin A. The chain length of the branched chain may be chosen from the range not exceeding 4. Preferably, the branched chain has 3 or less carbon atoms; in particular, methyl group ($CH_3$—) or methylidene group ($CH_2$=) having one carbon atom is more preferable. The main chain of $R_4$ may be a saturated alkylene group or an unsaturated alkenylene or alkadienylene group. If $R_4$ has amethylidene group ($CH_2$=) as the branched chain, it will have more unsaturated carbon-carbon bonds than the aforementioned main chain. However, if an unsaturated carbon-carbon bond is to be present in the main chain, it may advantageously be take the trans configuration relative to the direction of the main chain.

Examples of the amino acids of the general formula (V) may include 2-aminoheptane-dioic acid (α-aminopimelic acid; H-Api-OH) as one having a tetramethylene group with 4 carbon atoms as $R_4$, 2-aminooctane-dioic acid (α-aminosuberic acid; H-Asu-OH) as one having a pentamethylene group with 5 carbon atoms as $R_4$, and 2-aminononane-dioic acid (α-aminoazelaic acid; H-Aaz-OH) as one having a hexamethylene group with 6 carbon atoms as $R_4$.

The remaining portion of the cyclic tetrapeptide plays such a role that the oxide chain hydroxamic acid structure: —$R_4$—CO—NH—OH derived from the amino acid of the aforementioned general formula (V) is directed to the enzymatically active site of histone deacetylase and held there. This role is substantially identical with the function of the cyclic peptide portion of trapoxin analogs which are known irreversible inhibitors. Thus, the remaining portion of the cyclic tetrapeptide provides intermolecular linkage to the neighborhood of the enzymatically active site of histone deacetylase, thereby ensuring that the side chain hydroxamic acid structure derived from the amino acid of the aforementioned general formula (V) is fixed onto the enzymatically active site.

Figure 2:
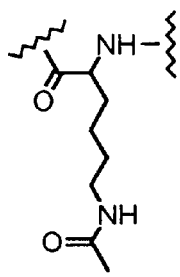
FIG. 2 shows the molecular structures of trapoxin analogs.
Figure 2:
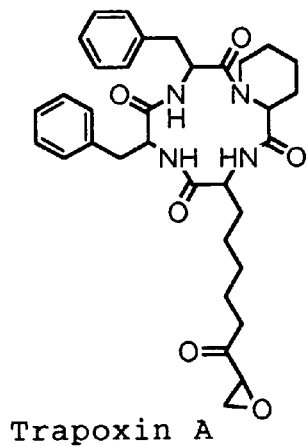
Figure 2:
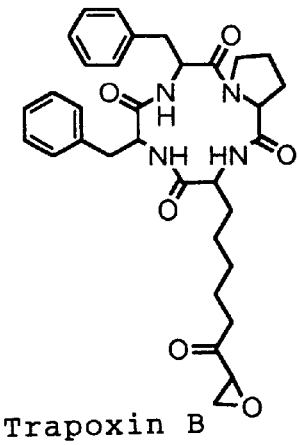
Figure 2:
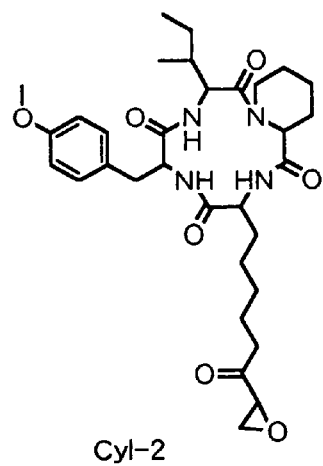
Figure 2:
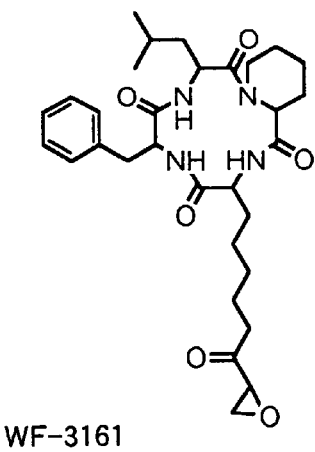
Figure 2:
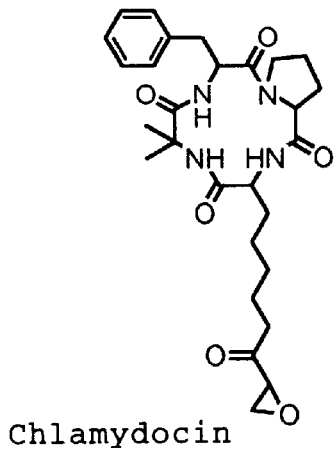
Figure 2:
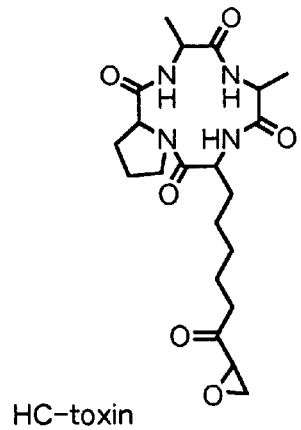

Therefore, the remaining three α-amino acids may be of any types so long as their side chains are utilized in binding the peptide to the surface of the histone deacetylase protein. The cyclic amino acid of the general formula (IV) is a main functional part for fixing the direction of the side chain hydroxamic acid structure derived from the amino acid of the aforementioned general formula (V). The ring structure of the cyclic amino acid of the general formula (IV) is preferably a 5-membered ring that is the same as the naturally occurring D-proline in trapoxin B shown in FIG. 2 or a 6-membered ring that is the same as the naturally occurring D-piperidine-2-carboxylic acid in trapoxin A shown in FIG. 2. Thus, the divalent group $R_3$ constituting this ring is preferably a trimethylene group in proline, a tetramethylene group in piperidine-2-carboxylic acid, or an unsaturated linear hydrocarbon group having a carbon-carbon double bond in correspondence to the linear hydrocarbon group with a chain length of 3 or 4. The aforementioned linear hydrocarbon group with a chain length of 3 or 4 may have a branched chain added on the chain; this branched chain may be replaced with a fused ring structure; or in these divalent hydrocarbon groups, the carbon atoms which form a bond to the amino nitrogen atom and the carbon atom at α position of the carboxylic acid and which are other than the carbon atom on which the free valence in said divalent group is present may be replaced with any heteroatom such as oxygen, sulfur or nitrogen. If the aforementioned branched chain is to be replaced with a fused ring structure, $R_3$ itself exists as a part of the ring in the cyclic amino acid of the general formula (IV). For example, 1,2,3,4-tetrahydroisoquinoline-3-carboxylic acid corresponds to a structure in which a benzene ring is fused to piperidine-2-carboxylic acid; as in this example, the ring structure of the cyclic amino acid may mean one in which two rings are fused. Inter alia, $R_3$ is more preferably a trimethylene group, a tetramethylene group, or an unsaturated linear hydrocarbon group having a carbon-carbon double bond in correspondence to the linear hydrocarbon group with a chain length of 3 or 4.

The present invention encompasses a variation in which the cyclic amino acid of the general formula (IV) is replaced with N-alkylated α-amino acid, such as N-methylglycine (sarcosine), having a similar structure except that the carbon chain forming the ring structure of said cyclic amino acid is interrupted. If the cyclic amino acid of the general formula (IV) is to be replaced with an N-alkylated α-amino acid having a similar structure, said N-alkylated α-amino acid preferably has a configuration equivalent to that of a cyclic amino acid having D-configuration. Therefore, the alkyl group used in N-alkylation is preferably a methyl or ethyl group: in particular, a methyl group is more preferable.

Generally, the remaining two α-amino acids preferably have a side chain as bulky as naturally occurring α-amino acids. That is to say, the side chain should not be more bulky than p-hydroxybenzyl group of tyrosine, benzyl group of phenylalanine or 3-indolylmethyl group of tryptophan in the trapoxin analogs shown in FIG. 2. As in the case of the corresponding portions of these trapoxin analogs, amino acids other than basic or acidic amino acids, i.e., neutral amino acids among hydrophobic amino acids and hydrophilic amino acids are preferable. Further, non-native amino acids having a structural similarity to neutral amino acids among naturally occurring hydrophobic amino acids and hydrophilic amino acids may be used. Therefore, preferred choices for $R_{11}$, $R_{12}$, $R_{21}$ and $R_{22}$ may include hydrogen, linear alkyl groups having 1 to 6 carbon atoms, branched alkyl groups having 3 to 6 carbon atoms, benzyl group, 4-methoxybenzyl group, 3-indolylmethyl group, (N-methoxy-3-indolyl)methyl group, (N-formyl-3-indolyl) methyl group, and a methyl group substituted with an aryl group having 4 or less rings which is similar to benzyl group. The methyl group substituted with an aryl group having 4 or less rings means a methyl group substituted with an aryl group in which 4 or less rings constitute a fused ring structure, such as 1-naphthyl group or 1-phenanthryl group, and corresponds to a benzyl group further fused with a benzene ring.

In addition, in the α-amino acid side chains represented by $R_{11}$, $R_{12}$, $R_{21}$ and $R_{22}$, those which are disubstituted on the amino group nitrogen atom contained therein may be used, as in the case of N,N-dimethylaminophenyl group present in trichostatin A shown in FIG. 1; alternatively, those in which the phenyl group in the benzyl group is replaced with a pyrimidyl group or a like substituent containing nitrogen atom in a heterocyclic aromatic ring group, may be used. Further, those in which the carboxyl group in the side chain is converted to an ester or amide may also be used.

As in the case of 2-methylalanine (2-amino-2-methylpropanoic acid; H-Aib-OH) present in chlamydocin shown in FIG. 2, a less bulky side chain may also be present on α position of a naturally occurring ordinary α-amino acid. Either one of $R_{11}$ or $R_{12}$ may advantageously be hydrogen atom, except for the case where they are less bulky side chains which do not cause steric interference as in 2-methylalanine. For the same reason, either one of $R_{21}$ or $R_{22}$ may advantageously be hydrogen. In particular, those amino acids which give benefit to hydrophobic interaction upon binding to proteins, as exemplified by naturally occurring hydrophobic amino acids and tyrosine, may more preferably be selected as the a-amino acids represented by the aforementioned general formulae (II) and (III). When hydroxyl or imino group is present as in tyrosine or tryptophan, said group may advantageously be protected by a suitable modification, such as O-alkylation of the hydroxyl group, N-alkoxylation of the imino group or N-acylation.

Therefore, a more preferred example of the cyclic tetrapeptide derivatives represented by the general formula (I) may be represented by the following general formula (VI):

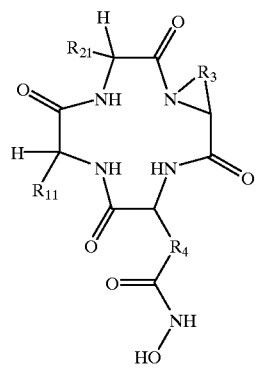

(VI)

wherein $R_{11}$ has the same meaning as $R_{11}$ in the general formula (I), $R_{21}$ a has the same meaning as $R_{21}$ in the general formula (I) $R_3$ has the same meaning as $R_3$ in the general formula (I), and $R_4$ has the same meaning as $R_4$ in the general formula (I), and $R_{11}$ and $R_{21}$ are more preferably selected from those which give benefit to hydrophobic interaction upon binding to proteins, as exemplified by naturally occurring hydrophobic amino acids and tyrosine. Illustratively, $R_{11}$ and $R_{21}$ in the general formula (VI) are more preferably selected from the benzyl group of phenylalanine, p-hydroxybenzyl group of tyrosine or its O-methylated form, p-methoxybenzyl group, the methyl group of alanine, 1-methylpropyl group of isoleucine, isopropyl group of valine, isobutyl group of leucine, hydrogen of glycine, and ethyl or propyl group. When $R_{11}$ is a group containing an aromatic ring, as exemplified by the aforementioned benzyl group or p-methoxybenzyl group, it is preferred to select $R_{21}$ from chained hydrocarbon groups. This combination also benefits the synthesis of said cyclic peptides.

In the cyclic tetrapeptide derivatives of the general formula (I') according to the present invention, the amino acid sequence forming the ring in the cyclic tetrapeptide derivatives of the general formula (I) is reversed and the amino acids of the general formulae (II) to (V) preferably selected for the cyclic tetrapeptide derivatives of the general formula (I) are also preferred for the cyclic tetrapeptide derivatives of the general formula (I'). With respect to the configurations of the amino acids of the general formulae (II) to (V), it is also more preferred to select D-configuration for the cyclic α-amino acid of the general formula (IV) and the α-amino acid of the general formula (II) while the remaining two α-amino acids take L-configuration or to its enantiomer.

The cyclic tetrapeptide derivatives of the general formula (I") according to the present invention correspond to the cyclic tetrapeptide derivatives of the general formula (I), except that the hydroxamic acid structure derived from the side chain carboxyl group of the a-amino acid represented by the general formula (V) is replaced with a structure similar to the structure of the N-acetylamino group in the side chain of the acetylated lysine residue in the substrate, acetylated histone. Therefore, the amino acids of the general formulae (II) to (IV) preferably selected for the cyclic tetrapeptide derivatives of the general formula (I) are also preferred as the amino acids of the general formulae (II) to (IV) in the cyclic tetrapeptide derivatives of the general formula (I"). With respect to the amino acid of the general formula (V'), in particular to the divalent group $R_4$ constituting the side chain thereof, those preferable as the divalent group $R_4$ derived from the amino acid of the general formula (V) in the cyclic tetrapeptide derivatives of the general formula (I) are also preferred. A particular difference from the amino acid of the general formula (V) is that in the amino acid of the general formula (V'), the chain length of the divalent group $R_4$ corresponding to the side chain of acetylated lysine residue is more preferably 4. Further, with respect to the configurations of the amino acids of the general formulae (II) to (IV) and (V'), selections preferable for the aforementioned cyclic tetrapeptide derivatives of the general formula (I) are also preferred. Consequently, a series of compounds in which the hydroxamic acid structure in the aforementioned general formula (VI), which is a preferred example of the cyclic tetrapeptide derivatives of the general formula (I), is replaced with N-acylated amino group structure are similarly preferred examples for the cyclic tetrapeptide derivatives of the general formula (I")

The cyclic tetrapeptide derivatives of the general formula (I") according to the present invention correspond to the cyclic tetrapeptide derivatives of the general formula (I), except that the hydroxamic acid structure derived from the side chain carboxyl group of the a-amino acid represented by the general formula (V) is replaced with a structure similar to the structure of the N-acetylamino group in the side chain of the acetylated lysine residue. in the substrate, acetylated histone. Therefore, the amino acids of the general formulae (II) to (IV) preferably selected for the cyclic tetrapeptide derivatives of the general formula (I) are also preferred as the amino acids of the general formulae (II) to (IV) in the cyclic tetrapeptide derivatives of the general formula (I"). With respect to the amino acid of the general formula (V') in particular to the divalent group $R_4$ constituting the side chain thereof, those preferable as the divalent group $R_4$ derived from the amino acid of the general formula (V) in the cyclic tetrapeptide derivatives of the general formula (I) are also preferred. Consequently, a series of compounds in which the hydroxamic acid structure in the aforementioned general formula (VI), which is a preferred example of the cyclic tetrapeptide derivatives of the general formula (I), is replaced with N-acylated amino group structure are similarly preferred examples for the cyclic tetrapeptide derivatives of the general formula (I").

The cyclic tetrapeptide derivatives of the general formula (I''') according to the present invention correspond to the cyclic tetrapeptide derivatives of the general formula (I'), except that the hydroxamic acid structure derived from the side chain carboxyl group of the α-amino acid represented by the general formula (V) is replaced with a structure similar to the structure of the N-acetylamino group in the side chain of the acetylated lysine residue in the substrate acetylated histone. Alternatively, they correspond to the cyclic tetrapeptide derivatives of the general formula (I"), except that the amino acid sequence forming the ring is reversed. Therefore, the amino acids of the general formulae (II) to (IV) preferably selected for the cyclic tetrapeptide derivatives of the general formula (I) are also preferred as the amino acids of the general formulae (II) to (IV) in the cyclic tetrapeptide derivatives of the general formula (I'''). With respect to the amino acid of the general formula (V'), in particular to the divalent group $R_4$ constituting the side chain thereof, those preferable as the divalent group $R_4$ derived from the amino acid of the general formula (V) in the cyclic tetrapeptide derivatives of the general formula (I) are also preferred. A particular difference from the amino acid of the general formula (V) is that in the amino acid of the general formula (V'), the chain length of the divalent group $R_4$ corresponding to the side chain of acetylated lysine residue is more preferably 4. Further, with respect to the configurations of the amino acids of the general formulae (II) to (V) and (V'), selections preferable for the aforementioned cyclic tetrapeptide derivatives of the general formula (I') is also preferred.

The cyclic tetrapeptide derivatives of the general formula (I''') according to the present invention correspond to the cyclic tetrapeptide derivatives of the general formula (I'), except that the hydroxamic acid structure derived from the side chain carboxyl group of the α-amino acid represented by the general formula (V) is replaced with a structure similar to the structure of the N-acetylamino group in the side chain of the acetylated lysine residue in the substrate acetylated histone. Alternatively, they correspond to the cyclic tetrapeptide derivatives of the general formula (I"), except that the amino acid sequence forming the ring is reversed. Therefore, the amino acids of the general formulae (II) to (IV) preferably selected for the cyclic tetrapeptide derivatives of the general formula (I) are also preferred as the amino acids of the general formulae (II) to (IV) in the cyclic tetrapeptide derivatives of the general formula (I'''). With respect to the amino acid of the general formula (V') in particular to the divalent group $R_4$ constituting the side chain thereof, those preferable as the divalent group $R_4$ derived from the amino acid of the general formula (V) in the cyclic tetrapeptide derivatives of the general formula (I) are also preferred.

The cyclic tetrapeptide derivatives of the present invention are any one of those of the general formulae (I) to (IV), in which the amino acid sequence forming the ring is the same or reverse. When the amino acid sequence is the same, the compounds of the general formula (I) are generally more preferable than the compounds of the general formula (I') and the compounds of the general formula (I") are more preferable than the compounds of the general formula (I'''). In a comparison between the compounds of the general formula (I) and the compounds of the general formula (I"), the compounds of the general formula (I) are generally more preferable if $R_4$ constituting the side chain of the amino acid residue of the general formula (V) is the same as $R_4$ constituting the side chain of the amino acid residue of the general formula (V'). As stated above, the cyclic tetrapeptide derivatives of the general formula (I) according to the present invention may be prepared by processes for the formation of peptide chain and cyclization using the four α-amino acids represented by the general formulae (II) to (V) as the starting materials. One example of the processes will be generally described below.

(Process for Preparation)

The cyclic tetrapeptide derivatives of the present invention may be prepared by first preparing a chained tetrapeptide intermediate in which the four α-amino acids represented by the general formulae (II) to (V) are linked through peptide linkage, then converting it to a cyclic tetrapeptide, and eventually derivatizing the side chain carboxyl group of the α-amino acid represented by the general formula (V) to a hydroxamic acid structure. Hereinbelow the process for the preparation will be generally described. The chained tetrapeptide intermediate may be used in a structure which is cleaved at any of the peptide linkages in the desired cyclic tetrapeptide derivative. In the description below, however, a synthesis route via a chained tetrapeptide intermediate having the cyclic α-amino acid represented by the general formula (IV) at the C-terminal and the α-amino acid represented by the general formula (V) at the N-terminal will be given as an example.

(Step 1) Synthesis of Chained di-, tri- and Tetrapeptides

First, according to a general procedure of peptide synthesis, amino acids of the general formulae (III) and (IV) are linked to each other, an amino acid of the general formula (II) is then linked, and finally an amino acid of the general formula (V) whose side chain carboxyl group has been protected by benzyl oetrification, e.g., L-Aaz(OBzl), L-Asu(OBzl) or L-Api(OBzl), is linked to form a chained tetrapeptide represented by the following general formula (VII):

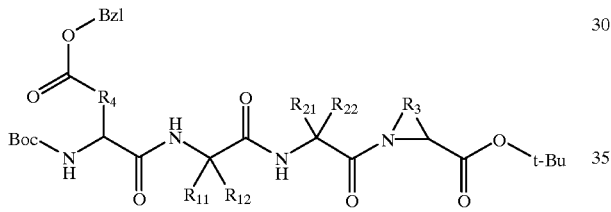

(VII)

wherein $R_{11}$, $R_{12}$, $R_{21}$, $R_{22}$, $R_3$ and $R_4$ have the same meanings as $R_{11}$, $R_{12}$, $R_{21}$, $R_{22}$, $R_3$ and $R_4$, respectively, of the general formula (I).

In this process, Boc or Z-group was used to protect the amino groups of the starting amino acids, tert-butyl ester was used to protect the caroboxyl groups, and condensation was effected by DCC/HOBt method. The Z-group was removed by catalytic reduction with Pd-C catalyst in acetic acid, which was then distilled off, followed by extraction of free amine with aqueous sodium bicarbonate into ethyl acetate. An oily product recovered from the extract was used in condensation subsequent to vacuum drying.

The entirely protected chained tetrapeptide represented by the general formula (VII) was purified by flash chromatography Using silica gel column.

(Step 2) Synthesis of Cyclic Peptide by Very High Dilution Method

Using trifluoroacetic acid, the Boc-group and tert-butyl ester in the entirely protected chained tetrapeptide represented by the general formula (VII) were removed (deprotected). After distilling off trifluoroacetic acid from the reaction mixture, the product represented by the following general formula (VIII):

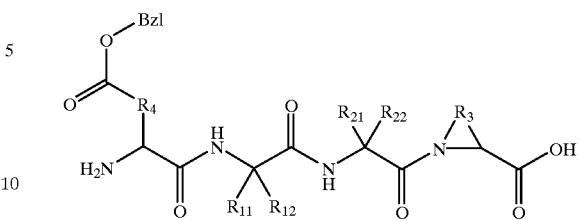

(VIII)

wherein $R_{11}$, $R_{12}$, $R_{21}$, $R_{22}$, $R_3$ and $R_4$ have the same meanings as $R_{11}$, $R_{12}$, $R_{21}$, $R_{22}$, $R_3$ and $R_4$, respectively, of the general formula (I) was solidified with ether and petroleum ether and vacuum dried.

One-tenth of the amount to be used of the peptide represented by the general formula (VIII) was dissolved in DMF and adjusted to a concentration of 0.1 mM. To the DMF solution under ice cooling, a tertiary amine, e.g., diisopropylethylamine, and HATU (O-(7-azabenzotriazol-1-yl)-1,1,3,3-tetramethyluronium hexafluorophosphate) were added, and stirred at room temperature for 30 minutes. Subsequently, ¹⁄₁₀ of the amount to be used of the peptide represented by the general formula (VIII) and HATU were added to the aforementioned DMP solution and stirred at room temperature for 30 minutes. These procedures were repeated 10 times in total to effect cyclization reaction. After the reaction, the reaction product (cyclic peptide) represented by the following general formula (IX):

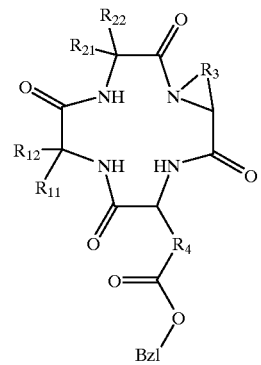

(IX)

wherein $R_{11}$, $R_{12}$, $R_{21}$, $R_{22}$, $R_3$ and $R_4$ have the same meanings as $R_{11}$, $R_{12}$, $R_{21}$, $R_{22}$, $R_3$ and $R_4$, respectively, of the general formula (I) was extracted into ethyl acetate and purified by flash chromatography using silica gel column.

(Step 3) Introduction of Side Chain Hydroxamic Acid Structure

The side chain benzyl ester of the cyclic peptide represented by the general formula (IX) was removed by catalytic reduction with Pd—C catalyst in methanol, and after distilling off methanol, vacuum drying was effected to yield an oily product as a carboxylic acid.

The cyclic peptide compound having a carboxylic acid on the side chain as obtained by the aforementioned deprotection and HOBt were dissolved in DMF, and under ice cooling, hydroxylamine hydrochloride, triethylamine and then BOP reagent were added and stirred for 1 hour. After the reaction, DMF was distilled off, decantation was performed with water, and then localization wag effected to yield a final product as a white powder. This white powder was dissolved in a small amount of methanol, purified using semi-preparative column in HPLC, and lyophilized to yield a desired product represented by the general formula (I).

The cyclic tetrapeptide derivatives represented by the general formula (I') according to the present invention may be prepared by a similar procedure: first, a chained tetrapeptide is synthesized according to the aforementioned Step 1, then converted into a cyclic tetrapeptide utilizing the conditions of Step 2; and the carboxyl group protected in the form of side chain benzyl ester etc. derived from the starting a-amino acid represented by the general formula (V) is converted into a side chain hydroxamic acid structure according to Step 3.

The cyclic tetrapeptide derivatives represented by the general formula (I") according to the present invention can be prepared by the following procedure: an α-amino acid represented by the general formula (V') is used instead of the a-amino acid represented by the general formula (V) to synthesize a chained tetrapeptide according to the aforementioned Step 1, then converted to a cyclic tetrapeptide using the conditions of Step 2. In these steps, the side chain amino group of the α-amino acid represented by said general formula (V') is protected with a generally used protecting group such as benzyloxycarbonyl group (Z group) for carried out the formation of a series of peptide linkages and cyclization reaction. Then, the protecting group on the side chain amino group of the α-amino acid represented by said general formula (V') in the resulting cyclic tetrapeptide is deprotected to form a hydrochloride. Thereafter, a desired acyl group is substituted and introduced onto the side chain amino group. For instance, the introduction of a desired acyl group can be performed by using a corresponding acid anhydride and carrying out a generally used N-acylation reaction.

The cyclic tetrapeptide derivatives represented by the general formula (I''') according to the present invention can also be prepared by a similar procedure: an α-amino acid represented by the general formula (V') is used instead of the α-amino acid represented by the general formula (V) to form a cyclic tetrapeptide structure as in the synthesis of the aforementioned cyclic tetrapeptide derivatives represented by the general formula (I'). Thereafter, the protecting group on the side chain amino group of the α-amino acid represented by said general formula (V') is deprotected to form a hydrochloride salt. Then, a desired acyl group is substituted and introduced onto the side chain amino group. This N-acylation reaction may be carried out according to the conditions for the cyclic tetrapeptide derivatives represented by the general formula (I").

In addition to the aforementioned synthesis methods, the compounds represented by the general formula (I) or the general formula (I') maybe synthesized by methods utilizing solid phase synthesis as illustrated in the below mentioned Examples 14, 18 and 23. For the compounds represented by the general formula (I") or the general formula (I'''), the extension of peptide chain and its cyclization may be carried out according to methods utilizing solid phase synthesis as illustrated in the below mentioned Examples 14 and 18.

The pharmaceutically acceptable salts of the cyclic tetrapeptide derivatives according to the present invention mean, for example, salts with pharmaceutically acceptable inorganic acids, such as hydrochlorides, and salts with pharmaceutically acceptable organic acids, such as acetate salts, if the derivatives contain a nitrogen atom showing basicity.

The MHC class-I molecule expression promoting agents of the present invention comprise as effective ingredients the cyclic tetrapeptide derivatives having a hydroxamic acid structure (hydroxyaminocarbonyl structure) at the side chain terminal as described above or the cyclic tetrapeptide derivatives having an N-acylated amino group structure at the side chain terminal, and the agents have excellent expression promoting activities as shown in the below-mentioned Test Examples. The MHC class-I molecule expression promoting action is ancillary to histone deacetylase enzyme inhibiting activity and this inhibition is considered to be reversible like trichostatin A having a hydroxamic acid structure. Further, not only by cell growth inhibition and cell cycle inhibiting action cue to histone deacetylase enzyme inhibition which becomes remarkable upon administration at higher concentrations, but also by the complementary effect of action in eliminating cancer cells or cancerizing virus infected cells associated with cytotoxic T cells due to promoted MHC class-I molecule expression, advantages of high therapeutic effects are provided. In addition, application as a drug is expected, which, when compared with trapoxin analogs which are irreversible inhibitors, allows unfavorable effects on the living body such as side-effects on normal tissue cells persist to a less degree and which, when compared with treating effects, cause greatly reduced relative side-effects.

The pharmaceutical composition of the present invention attains therapeutic effects by utilizing the aforementioned MHC class-I molecule expression promoting action; the dose of the cyclic tetrapeptide derivative as an effective ingredient may be appropriately determined depending upon the object of the treatment, the degree of symptoms, the sex, age and body weight of a subject to be treated by its administration. When an adult male is to be treated, the daily dose is usually in the range of 0.1 to 50 mg/kg, preferably 0.5 to 10 mg/kg; this dose is preferably divided into several portions per day. The pharmaceutical composition may be made in any dosage form suitable for its administration route and to this end, additive(s) which are generally used for peptide-like compound preparations of this type may be added to the cyclic tetrapeptide derivative as an effective ingredient. Since the composition is high in cell permeability, a variety of administration routes can be used; dosage forms and administration routes commonly used to administer peptide hormones are preferred.

The cyclic tetrapeptide derivatives of the present invention and processes for the preparation thereof as well as excellent physiological activities of said cyclic tetrapeptide derivatives, i.e., excellent MHC class-I molecule expression promoting action and histone deacetylase enzyme inhibiting activity, will be described by way of examples.

EXAMPLE 1

HDA-5; cyclo(-Asu(NHOH)-Phe-Phe-D-Pro-)

The process for the synthesis of the cyclic tetrapeptide HDA-5; cyclo(-Asu(NHOH) -Phe-Phe-D-Pro-) represented by the following formula (X):

19

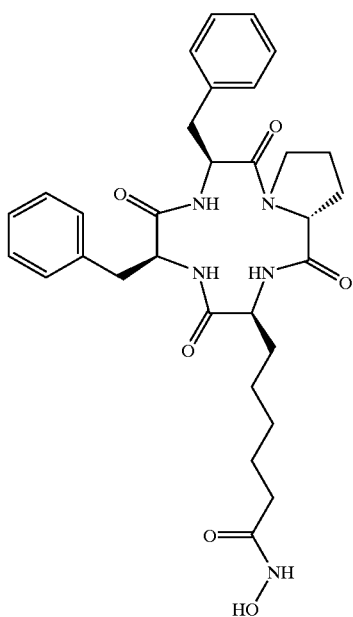

(X)

will be described step by step.
Synthesis of cyclo(-Asu(NHOH)-Phe-Phe-D-Pro-)
Step 1-1: Z-Phe-D-Pro-OtBu To a solution Qf Z-phe-OH (874 mg, 2.92 mmol), H-Pro-OtBu (500 mg, 2.92 mmol) and HOBt.H$_2$O (490 mg, 3.20 mmol) in DMF (15 ml), DCC (660 mg, 3.20 mmol) was added under ice cooling and stirred for 1 hour and further stirred overnight at room temperature. After the reaction mixture wag filtered and concentrated, it was redissolved in ethyl acetate and washed sequentially with 10% citric acid, 4% NaHCO$_3$ and with saturated aqueous sodium chloride solution. After being dried over anhydrous MgSO$_4$ and concentrated, the residue was purified by flash silica gel chromatography (CHCl$_3$) to yield 1.40 g (quant) of the titled dipeptide compound as an oily material.

Rf=0.72 (CHCl$_3$/MeOH=9/1)

Step 1-2: Z-Phe-Phe-D-Pro-OtBu

The dipeptide compound Z-Phe-D-Pro-OtBu (700 mg, 1.45 mmol) obtained in step 1-1 was dissolved in acetic acid (5 ml) and stirred overnight (about 14 hours) under hydrogen atmosphere in the presence of 5% Pd/C (70 mg). After the reaction mixture was filtered and concentrated, an oily residue was dissolved in ethyl acetate and washed with 4% NaHCO$_3$. After being dried over anhydrous sodium carbonate, the product was concentrated to yield H-Phe-D-Pro-OtBu (425 mg, 92%). The concentrate was redissolved in DMF (5 ml), and Z-Phe-OH (434 mg, 1.45 mmol) and HOBt. H$_2$O (245 mg, 1.60 mmol) were added, followed by adding DCC (230 mg, 1.60 mmol) under ice cooling, and as such the mixture was stirred overnight. The reaction mixture was filtered, concentrated, redissolved in ethyl acetate, and washed sequentially with 10% citric acid, 4% NaHCO$_3$ and with saturated aqueous sodium chloride solution. After being dried over MgSO$_4$ and concentrated, the residue was purified by flash silica gel chromatography (CHCl$_3$) to yield 720 mg (90%) of the titled tripeptide compound as a foamy material.

Rf=0.52 (CHCl$_3$/MeOH=9/1)

20

Step 1-3: Boc-Asu(OBzl)-Phe-Phe-D-Pro-OtBu

The tripeptide compound Z-Phe-Phe-D-Pro-OtBu (422 mg, 0.704 mmol) obtained in step 1-2 was dissolved in acetic acid (5 ml) and stirred overnight (about 14 hours) under hydrogen atmosphere in the presence of 5% Fd/C (40 mg). After the reaction mixture was filtered and concentrated, an oily residue was dissolved in ethyl acetate and washed with 4% NaHCO$_3$. After being dried over anhydrous sodium carbonate, the product was concentrated to yield H-Fhe-Phe-D-Fro-OtBu (302 Mg, 92%).

The concentrate was redissolved in DMF (5 ml), and Boc-Asu(OBzl)-OH (320 mg, 0.844 mmol) and HOBt. H$_2$O (142 mg, 0.844 mmol) were added, followed by adding DCC (192 mg, 0.928 mmol) under ice cooling, and as such the mixture was stirred overnight. The reaction mixture was filtered, concentrated, redissolved in ethyl acetate, and washed sequentially with 10% citric acid, 4% NaHCO$_3$ and with saturated aqueous sodium chloride solution. After being dried over MgSO$_4$ and concentrated, the residue was purified by flash silica gel chromatography (CHCl$_3$) to yield 426 mg (80%) of the titled linear tetrapeptide compound as a foamy material.

Rf=0.59 (CHCl$_3$/MeOH=9/1)

HPLC: Rt=23.5 min (column: Wako Pak C4, 4.6×150 mm, 37–100% linear gradient CH$_3$CN/0.1% TFA over 30 min)

Step 1-4: H-Asu(OBzl)-Phe-Phe-D-Pro-OH.TFA

To the compound Boc-Asu(OBzl)-Phe-Phe-D-Pro-OtBu (426 mg, 0.52 mmol) obtained in step 1-3, TFA (2 ml) was added and stirred under ice cooling for 2 hours. The reaction mixture was concentrated and ether/petroleum ether (1/5) was added to the residue to precipitate it so as to yield the titled compound (366 mg, 90%) as a white powder.

Rf=0.47 (CHCl$_3$/MeOH/AcOH=90/10/2)

HPLC: Rt=10.32 min (conditions being the same as in step 1-3)

FAB-MS: m/z-=671 (M+1)

Step 1-5; cyclo(-Asu(OBzl)-Phe-Phe-D-Pro-)

To a solution in DMA (400 ml) of the compound H-Asu(OBzl)-Phe-Phe-D-Pro-OH.TFA (31mg, 0.040 mmol) obtained in step 1-4, HATU (23 mg, 0.060 mmol) and 10% DIEA/DMF (280 µl, 0.16 mmol) were added and stirred at room temperature for 30 minutes. Further, the compound H-Asu(OBzl)-Phe-Phe-D-Pro-OH.TFA (31 mg, 0.040 mmol), HATU (23 mg, 0.060 mmol) and 10% DIEA/DMF (280 µl, 0.16 mmol) were added 9 times every 30 minutes. After the reaction mixture was concentrated, the residue was redissolved in ethyl acetate, washed sequentially with 10% citric acid, 4% NaHCO$_3$ and with saturated aqueous sodium chloride solution, dried over MgSO$_4$ and concentrated. The resulting residue was purified by silica gel chromatography (2.5% methanol/CHCl$_3$) to yield the titled cyclic tetrapeptide compound (220 mg, 84%) as an oily material.

HPLC: Rt=14.20 min (conditions being the same as in step 1-3)

Step 1-6: cyclo(-Asu(OH)-Phe-Phe-D-Pro-)

The compound cyclo(-Asu(OBzl)-Phe-Phe-D-Pro-) (94 mg, 0.144 mmol) obtained in step 1-5 was dissolved in MeOH (3 ml) and stirred for 4 hours under hydrogen atmosphere in the presence of 5% Pd/C (10 mg). By filtering and concentrating the reaction mixture, the titled compound (74 mg, 91%) was obtained as an oily material.

HPLC: Rt=17.03 min (column: Wako Pak C18, 4.6×150 mm, 10–100% linear gradient CH$_3$CN/0.1% TFA over 30 min)

Step 1-7: cyclo(-Asu(NHOH)-Phe-Phe-D-Pro-)

To a DMF (3 ml) solution of the compound cyclo(-Asu(OH)-Phe-Phe-D-Pro-) (74 mg, 0.132 mmol) obtained in step 1-6 and HOEt. H$_2$O (30 mg, 0.198 mmol), a filtrate obtained by adding TEA (40 μl, 0.264 mmol) to a solution of hydroxylamine hydrochloride (19 mg, 0.264 mmol) in DMF, neutralizing and filtering, and BOP (90 mg, 0.178 mmol) were added under ice cooling, and stirred for 3 hours. After being dried, the reaction mixture wag dissolved in MeOH, preparatively purified by reverse-phase HPLC (column: YMC-Pack ODS A323, 10×250 mm, 25% CH$_3$CN/0.1% TFA), and lyophilized to yield the titled compound.

HPLC: Rt=16.43 min (conditions being the same as in step 1-6)

FAB-MS: m/z=577 (M$^+$)

EXAMPLE 2

HDA-17; cyclo(-Aaz(NHOH)-Phe-Phe-D-Pro-)

The process for the synthesis of the cyclic tetrapeptide HDA-17; cyclo(-Aaz(NHOH)-Phe-Phe-D-Pro-) represented by the following formula (XI):

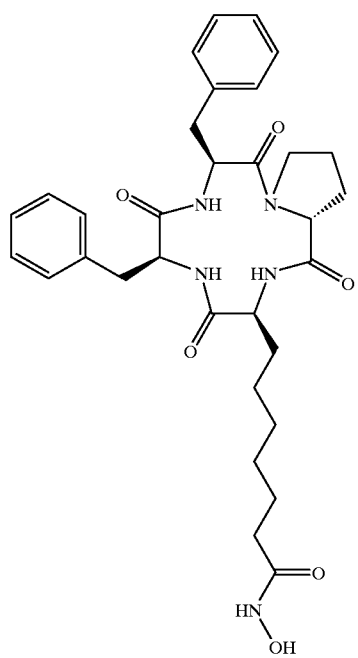

(XI)

will be briefly described. Subsequent to step 1-2 described in Example 1, a chained tetrapeptide Boc-Aaz(OBzl)-Phe-Phe-D-Pro-OtBu was prepared using Boc-Aaz(OBzl)-OH instead of Boc-Asu(OBzl)-OH according to step 1-3. Thereafter, by applying the procedure consisting of steps 1-4 to 1-7, deprotection, cyclization and conversion of the side chain carboxylic acid into hydroxamic acid structure (hydroxyaminocarbonyl structure) were carried out to yield the titled cyclic tetrapeptide.

FAB-MS: m/z=591 (M$^+$)

EXAMPLE 3

HDA-18; cyclo(-Api(NHOH)-Phe-Phe-D-Pro-)

The process for the synthesis of the cyclic tetrapeptide HDA-18; cyclo(-Api(NHOH)-Phe-Phe-D-Pro-) represented by the following formula (XII):

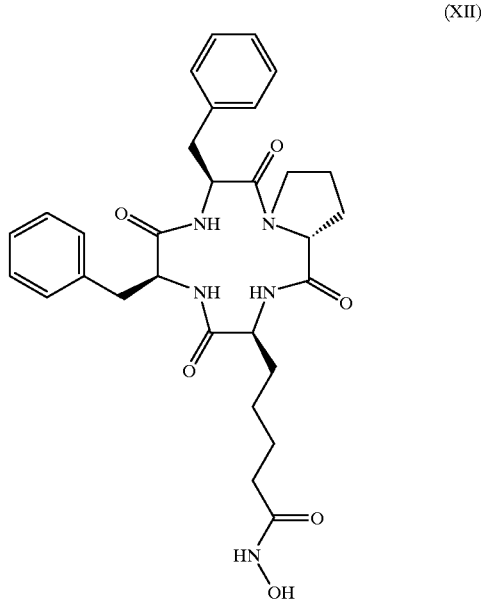

(XII)

will be briefly described. Subsequent to step 1-2 described in Example 1, a chained tetrapeptide Boc-Api(OBzl)-Phe-Phe-D-Pro-OtBu was prepared using Boc-Api(OBzl)-OH instead of Boc-Asu(OBzl)-OH according to step 1-3. Thereafter, by applying the procedure consisting of steps 1-4 to 1-7, deprotection, cyclization and conversion of the side chain carboxylic acid into hydroxamic acid structure (hydroxyaminocarbonyl structure) were carried out to yield the titled cyclic tetrapeptide.

FAB-MS: m/z=563 (M$^+$)

EXAMPLE 4

HDA-12; cyclo(-Asu(NHOH)-D-Phe-Leu-Pip-)

The process for the synthesis of the cyclic tetrapeptide HDA-12; cyclo(-Asu(NHOH)-D-Phe-Leu-Pip-) represented by the following formula (XIII):

(XIII)

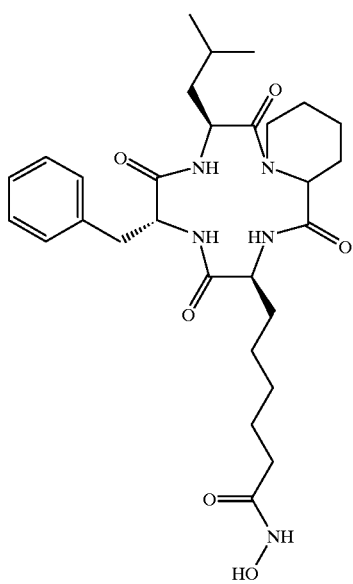

(XIV)

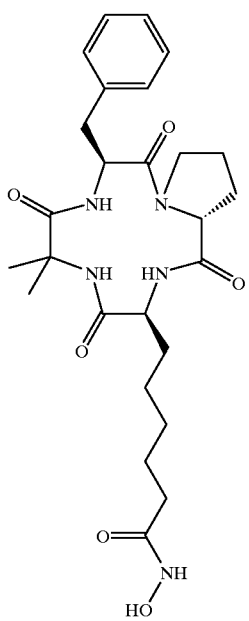

will be briefly described. According to step 1-1 of Example 1, Z-Leu-DL-Pip-OtBu was prepared from Z-Leu-OH and H-DL-Pip-OtBu. According to step 1-2 of Example 1, Z-D-Phe-Leu-DL-Pip-OtBu was prepared from Z-Leu-DL-Pip-OtBu and Z-D-Phe-OH. Then, a chained tetrapeptide Boc-Asu(OBzl)-D-Phe-Leu-DL-Pip-OtBu was obtained from Z-D-Phe-Leu-DL-Pip-OtBu and Boc-Asu(OBzl)-OH according to step 1-3 of Example 1. Thereafter, by applying the procedure consisting of steps 1-4 to 1-7, deprotection, cyclization and conversion of the side chain carboxylic acid into hydroxamic acid structure (hydroxyaminocarbonyl structure) were carried out to yield the titled cyclic tetrapeptide.

FAB-MS: m/z=559 (M$^+$)

EXAMPLE 5

HDA-15; cyclo(-Asu(NHOH)-Aib-Phe-D-Pro-)

The process for the synthesis of the cyclic tetrapeptide HDA-15; cyclo(-Asu(NHOH)-Aib-Phe-D-Pro-) represented by the following formula (XIV):

will be briefly described. Subsequent to step 1-1 of Example 1, Z-Aib-Phe-D-Pro-OtBu was prepared using Z-Aib-OH instead of Z-Phe-OH according to step 1-2. Then, a chained tetrapeptide Boc-Asu(OBzl)-Aib-Phe-D-Pro-OtBu was obtained from Z-Aib-Phe-D-Pro-OtBu and Boc-Asu(OBzl)-OH according to step 1-3. Thereafter, by applying the procedure consisting of steps 1-4 to 1-7, deprotection, cyclization and conversion of the side chain carboxylic acid into hydroxamic acid structure (hydroxyaminocarbonyl structure) were carried out to yield the titled cyclic tetrapeptide.

FAB-MS: m/z=517 (M$^+$)

Reference Example 1

HDA-19; cyclo(-Asu(NHOH)-Phe-Phe-D-Pro-)$_2$

The cyclic octapeptide HDA-19; cyclo(-Asu(NHOH)-Phe-Phe-D-Pro-)$_2$ in which the same amino acid sequence as in the tetrapeptide (HDA-5) of the aforementioned Example 1 is repeated, was prepared according to a similar procedure from Boc-Asu(OBzl)-Phe-Phe-D-Pro-OtBu obtained in step 1-3 of Example 1.

EXAMPLE 6 synthesis of HDA-13; cyclo(-L-Asu(NHOH)-D-Pro-L-Ala-D-Ala-)

The process for the synthesis of the cyclic tetrapeptide HDA-13; cyclo(-L-Asu(NHOH)-D-Pro-L-Ala-D-Ala-) represented by the following formula (XV):

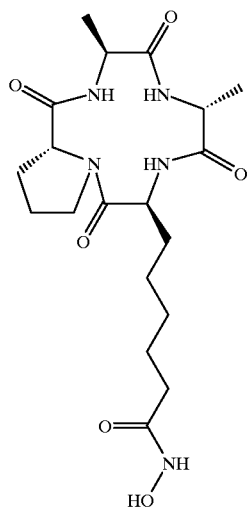

(XV)

will be briefly described.

Step 6-1: Boc-L-Asu(OBzl)-D-Pro-OtBu

Boc-L-Asu(OBzl)-OH (1.14 g, 3.0 mmol), H-D-Pro-OtBu (510 mg, 3.0 mmol) and HOBt.H$_2$O (505 mg, 3.3 mmol) were dissolved in DMF (7 ml), and DCC (681 mg, 3.3 mmol) was added under ice cooling and stirred overnight at room temperature. After being filtered and concentrated, the reaction mixture was redissolved in ethyl acetate and washed sequentially with 10% citric acid, 4% NaHCO$_3$ and with saturated aqueous sodium chloride solution. After being dried over anhydrous MgSO$_4$ and concentrated, the residue was purified by flash silica gel chromatography (CHCl$_3$) to yield 1.51 g (94%) of the titled compound as an oily material.

Rf=0.61 (CHCl$_3$/MeOH=9/1)

Step 6-2: Boc-L-Ala-D-Ala-OH

To an aqueous solution (5 ml) of H-D-Ala-OH (668 mg, 7.5 mmol), TEA (1.26 ml, 9.0 mmol) was added under ice cooling, followed by mixing with a solution (10 ml) of Boc-L-Ala-Osu (1.43 g, 5.0 mmol) in DMF and stirring overnight at room temperature. After concentration of the reaction mixture, the residue was dissolved in aqueous NaHCO$_3$ solution and the aqueous phase was washed with ethyl acetate. The aqueous phase was acidified with citric acid and extracted with ethyl acetate and the organic phase was washed with saturated aqueous sodium chloride solution. After drying over anhydrous MgSO$_4$ and concentrating, diethyl ether/petroleum ether (1/5) was added to the residue to solidify it, yielding 890 mg (68%) of the titled compound as a white powdery material.

Rf=0.40 (CHCl$_3$/MeOH/acetic acid=90/10/2)

Step 6-3 Boc-L-Ala-D-Ala-Asu(OBzl)-D-Pro-OtBu

To Boc-L-Asu(OBzl)-D-Pro-OtBu (1.4 g, 2.63 mmol), TFA (3 ml) was added under ice cooling, and the mixture was allowed to stand for 2 0Minuteg. The reaction mixture was concentrated and diethyl ether/petroleum ether (1/5) was added to the residue. Decantation yielded in H-L-Asu (OBzl)-D-Pro-OtBu TFA (2.0 g, quant).

This product was dissolved in DMF(10 ml) and Boc-L-Ala-D-Ala-OH (810 mg, 3.16 mmol) and HOBt H$_2$O (582 mg, 3.8 mmol) were added and further DCC (783 mg, 3.8 mmol) was added under ice cooling followed by stirring overnight. After filtering and concentrating, the reaction mixture was redissolved in ethyl acetate, and washed sequentially with 10% citric acid, 4% NaHCO$_3$ and with saturated aqueous sodium chloride solution. After drying over anhydrous MgSO$_4$ and concentrating, the residue was purified by flash silica gel chromatography (1% MeOH/CHCl$_3$) to yield 1.23 g (69%) of the titled compound as an oily material.

Rf=0.33 (CHCl$_3$/MeOH=9/1)

Step 6-4 cyclo(-L-Asu(NHOH)-D-Pro-L-Ald-D-Ala-)

Subsequently, by applying the procedure consisting of steps 1-4 to 1-7 of Example 1 (HDA-5), deprotection, cyclization and conversion of the side chain carboxylic acid into hydroxamic acid structure (hydroxyaminocarbonyl structure) were carried out to yield the titled cyclic tetrapeptide.

HPLC: Rt=8.22 min (column: Wako Pak C18, 4.6×150 mm, 0–100% linear gradient CH$_3$CN/0.1% TFA over 30 min, flow rate 1.0 ml/min)

FAB-MS: m/z=426 (M+H)$^+$

EXAMPLE 7

HDA-16; cyclo(-L-Asu(NHOH)-L-Trp(CHO)-L-Leu-D-Pip-)

The synthesis of the titled cyclic tetrapeptide HDA-16; cyclo(-L-Asu(NHOH)-L-Trp(CHO)-L-Leu-D-Pip-) represented by the following formula (XVI):

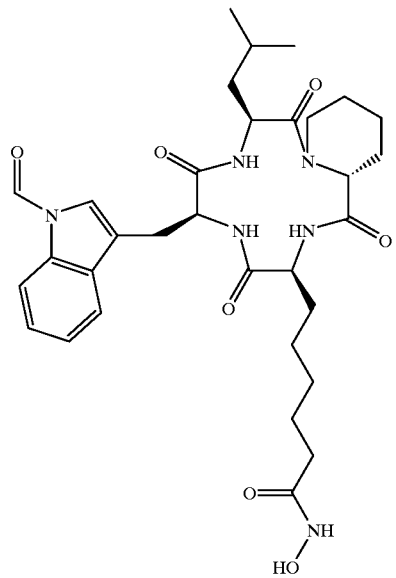

(XVI)

was carried out according to the procedure described in Example 4 (HDA-12)

HPLC: Rt=17.34 min (column: Wako Pak C18, 4.6×150 mm, 10–100% linear gradient CH$_3$CN/0.1% TFA over 30 min, flow rate 1.0 ml/min)

FAB-MS: m/z=647 (M+Na)$^+$

EXAMPLE 8

HDA-33; cyclo(-L-Asu(NHOH)-L-Trp-L-Leu-D-Pip-)

The synthesis of the titled cyclic tetrapeptide HDA-33; cyclo(-L-Asu(NHOH)-L-Trp-L-Leu-D-Pip-) represented by the following formula (XVII):

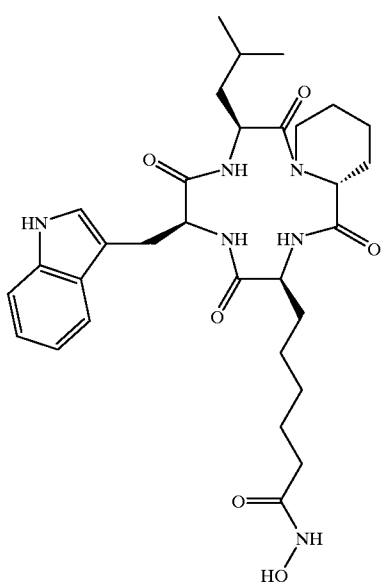

(XVII)

was carried out according to the procedure described in Example 4 (HDA-12).

HPLC: Rt=17.08 min (column: Wako Pak C18, 4.6×150 mm, 0–100% linear gradient $CH_3CN/0.1\%$ TFA over 30 min, flow rate 1.0 ml/min FAB-MS: m/z=597 $(M+H)^+$

EXAMPLE 9

HDA-32; cyclo(-L-Asu(NHOH)-L-Lys(Boc)-L-Phe-D-Pro-)

The process for the synthesis of the cyclic tetrapeptide HDA-32; cyclo(-L-Asu(NHOH)-L-Lys(Boc)-L-Phe-D-Pro-) represented by the following formula (XVIII):

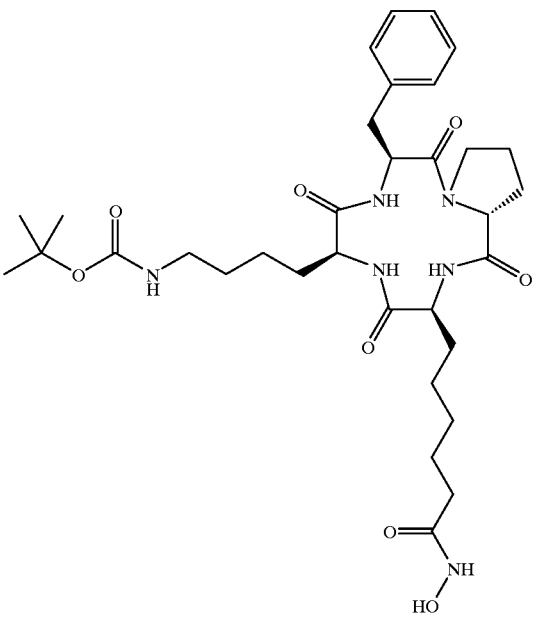

(XVIII)

will be briefly described.

Step 9-1 Boc-L-Asu(OBzl)-L-Lys(Z)-L-Phe-D-Pro-OtBu

Boc-L-Lys(Z)-L-Phe-D-Pro-OtBu was obtained according to steps 1-1 and 1-2 of Example 1 (HDA-5). To this tripeptide (1.96 g, 2.88 mmol), TFA (3 ml) was added under ice cooling, and the mixture was allowed to stand for 20 minutes. The reaction mixture was concentrated, dissolved in ethyl acetate, and washed sequentially with 4% $NaHCO_3$ and saturated aqueous sodium chloride solution. By drying over anhydrous $Na_2CO_3$ and concentrating, H-L-Lys(Z)-L-Phe-D-Pro-OtBu (1.32 g, 79%) was obtained.

This product was dissolved in DMF(10 ml) and, Boc-L-Asu(Otzl)-OH (1.07, 2.81 mmol) and HOBt $H_2O$ (502 mg, 3.28 mmol) were added and further DCC (677 mg, 3.28 mmol) was added under ice cooling followed by stirring overnight. After filtering and concentrating, the reaction mixture was redissolved in ethyl acetate, and washed sequentially with 10% citric acid, 4% $NaHCO_3$ and with saturated aqueous sodium chloride solution. After drying over anhydrous $MgSO_4$ and concentrating, the residue was purified by flash silica gel chromatography (1% MeOH/ $CHCl_3$) to yield 1.55 g (72%) of the titled compound as a foamy material.

Rf=0.80 ($CHCl_3$/MeOH=9/1)

Step 9-2 cyclo(-L-ASu-L-LyS(Boc)-L-Phe-D-Pro-)

To the compound Boc-L-Asu(OBzl)-L-Lys(Z)-L-Phe-D-Pro-OtBu obtained in step 9-1, the procedure consisting of steps 1-4 to 1-6 of Example 1 (HDA-5) was applied to carry out removal of Boc group and cyclization. The resulting protected cyclic tetrapeptide (98 mg, 0.128 mmol) was dissolved in acetic acid (3 ml) and stirred under hydrogen atmosphere for 4 hours using 5% Pd—C (30 mg). The reaction mixture was filtered and concentrated to yield cyclo(-L-Asu-L-Lys-L-Phe-D-Pro-).

This product was dissolved in a mixed solvent of dioxane (2 ml) and water (2 ml) and adjusted to pH 8 with NaHCO$_3$. A solution of Boc$_2$O (42 mg) in dioxane was added to the mixture, under ice cooling, followed by stirring overnight. After being concentrated, the reaction mixture was redissolved in ethyl acetate, and washed sequentially with 10% citric acid and saturated aqueous sodium chloride solution. After drying over anhydrous MgSO$_4$, concentration was effected to yield 61 mg (74%) of the titled compound.

Step 9-3 cyclo(-L-Asu(NHOH)-L-Lys(Boc)-L-Phe-D-Pro-)

Subsequently, by applying the procedure of step 1-7 of Example 1 (HDA-5), conversion of the side chain carboxylic acid into hydroxamic acid structure (hydroxyaminocarbonyl structure) was carried out to yield the titled cyclic tetrapeptide.

HPLC: Rt=17.51 min (column: Wako Pak C18, 4.6×150 mm, 10–100% linear gradient CH$_3$CN/0.1% TFA over 30 min, flow rate 1.0 ml/min)

FAB-MS: m/z=659 (M+H)$^+$

EXAMPLE 10

HDA-6; cyclo(-L-Lys(Ac)-L-Phe-L-Phe-D-Pro-)

The process for the synthesis of the cyclic tetrapeptide HDA-6; cyclo(-L-Lys(Ac)-L-Phe-L-Phe-D-Pro-) represented by the following formula (XIX):

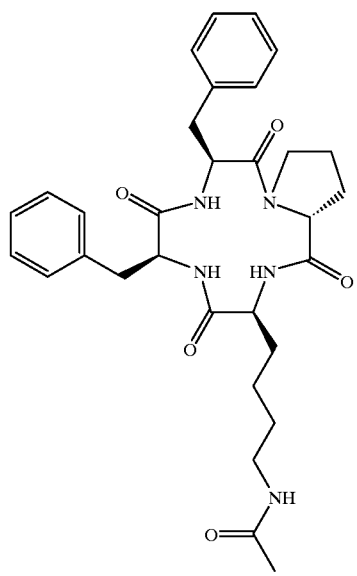

(XIX)

will be briefly described.

Step 10-1 cyclo (-L-Lys-L-Phe-L-Phe-D-Pro-).H(SEQ. ID NO: 1)

Cyclo(-L-Lys(Z)-L-Phe-L-Phe-D-Pro-) was obtained by the application of the procedure consisting of steps 1-1 to 1-6 described in Example 1 (HDA-5). After catalytic reduction in acetic acid, the acetate salt was converted into a hydrochloride to yield the titled compound.

FAB-MS: m/z=556 (M+H)$^+$

Step 10-2 cyclo(-L-Lys(Ac)-L-Phe-L-Phe-D-Pro-)

To a DMF (2 ml) solution of the cyclo(-L-Lys-L-Phe-L-Phe-D-Pro-).HCl (44 mg, 80 mmol) obtained in step 10-1, TEA(33 ml, 0.24 mmol) and acetic anhydride (12 ml, 0.12 mmol) were added under ice cooling and stirred for 2 hours. The reaction mixture was neutralized by addition of acetic acid and concentrated. The crude peptide was preparatively purified by reverse-phase HPLC (column: YMC-Pack ODS A-323, 10×250 mm, 30% CH$_3$CH/0.1% TFA) and lyophilized to yield 57 mg (quant) of the titled compound.

HPLC: Rt=16.68 min (column: Wako Pak C18, 4.6×150 mm, 10–100% linear gradient CH$_3$CN/0.1% TFA over 30 min, flow rate 1.0 ml/min)

FAB-MS: m/z=562 (M+H)$^+$

EXAMPLE 11

HDA-26; cyclo(-L-Lys(BrAc)-L-Phe-L-Phe-D-Pro-)

The process for the synthesis of the cyclic tetrapeptide HDA-26; cyclo(-L-Lys(SrAc)-L-Phe-L-Phe-D-Pro-) represented by the following formula (XX):

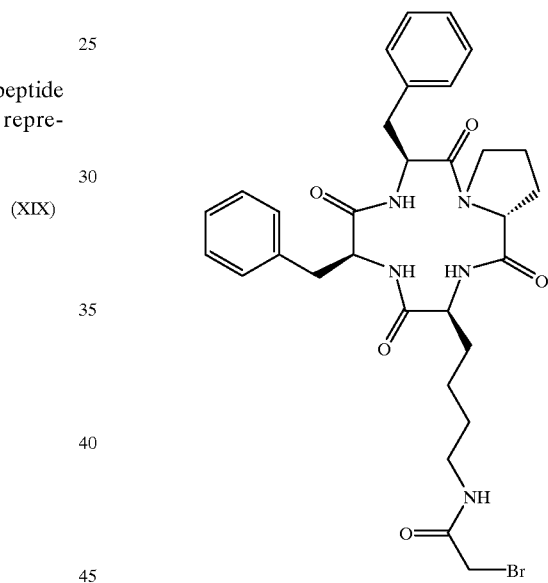

(XX)

will be briefly described.

Cyclo(-L-Lys-L-Phe-L-Phe-D-Pro-) HCl (50 mg, 90 mmol) obtained by the application of step 10-1 of Example 10 (HDA-6) and bromoacetic acid (19 mg, 0.135 mmol) were dissolved in DMF (1 ml), and TEA (19 ml, 0.135 mmol) and DCC (28 mg, 0.135 mmol) were added under ice cooling followed by stirring overnight. After filtering and concentrating, the reaction mixture was redissolved in ethyl acetate and washed sequentially with 10% citric acid, 4% NaHCO$_3$ and with aqueous saturated sodium chloride. After drying over anhydrous MgSO$_4$ and concentrating, the residue was purified by silica gel chromatography to yield 36 mg (62%) of the titled compound as an oily material.

HPLC: Rt=17.62 min (column: Wako Pak C18, 4.6×150 mm, 10–100% linear gradient CH$_3$CN/0.1% TFA over 30 min, flow rate 1.0 ml/min)

FAB-MS: m/z=640 (M+H)$^+$, 642 (M+3)$^+$

EXAMPLE 12

HAD-34; cyclo (-L-Glu(Gly-NHOH)-D-Tyr(Me)-L-Ile-D-Pro-)

The process for the synthesis of the cyclic tetrapeptide HDA-34; cyclo(-L-Glu(Gly-NHOH)-D-Tyr(Me)-L-Ile-D-Pro-) represented by the following formula (XXI):

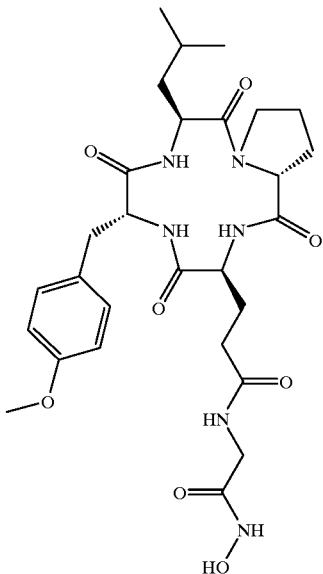

(XXI)

will be briefly described.

Step 12-1 Boc-L-Glu-OAll

To a solution of Boc-L-Glu-OH (2.47 g, 10.0 mmol) in THF (20 ml), DCC (2.27 g, 11.0 mmol) was added under ice cooling, followed by stirring for 2 hours. The reaction mixture was filtered and allyl alcohol (1.02 ml, 20.0 mmol) and dicyclohexylamine (2.39 ml, 12.0 mmol) were added to the filtrate, followed by stirring overnight. The reaction mixture was concentrated and washed with ether-petroleum ether to yield 3.90 g (83%) of the titled compound as a white powdery material.

Rf=0.74 ($CHCl_3$/MeOH/acetic acid=90/10/0.2)

Step 12-2 Boc-L-Glu(Gly-OBzl)-OAll

Boc-L-Glu-OAll DCHA (1.62 g, 3.45 mmol) obtained in step 12-1 was dissolved in ethyl acetate (200 ml) and washed sequentially with 10% citric acid and then with aqueous saturated sodium chloride. By drying over anhydrous $MgSO_4$ and concentrating, Boc-L-Glu-OAll was obtained.

Boc-L-Glu-OAll (630 mg, 2.19 mmol), H-Gly-OBzl TosOH(739 mg, 2.19 mmol and HOBt $H_2O$ (34 mg, 0.22 mmol) were dissolved in DMF (10 ml), and TEA (0.31 ml, 2.19 mmol) and DCC (543 mg, 2.63 mmol) were added under ice cooling, followed by stirring overnight at room temperature. After filtering and concentrating, the reaction mixture was redissolved in ethyl acetate and washed sequentially with 10% citric acid, 4% $NaHCO_3$ and aqueous saturated sodium chloride. After drying over anhydrous $MgSO_4$ and concentrating, purification was effected by flash silica gel chromatography (1% MeOH/$CHCl_3$) to yield 343 mg (46%) of the titled compound as an oily material.

HPLC: Rt=23.75 min (column: Wako Pak C18, 4.6×150 mm, 10–100% linear gradient $CH_3CN$/0.1% TFA over 30 min, flow rate 1.0 ml/min)

Step 12-3 Boc-L-Ile-D-Pro-OBzl

Boc-L-Ile-OH 1/2 $H_2O$ (1.13 g, 4.7 mmol), H-D-Pro-OBzl HCl (1.14 g, 4.7 mmol) and HOBt $H_2O$ (72 mg, 0.47 mmol) were dissolved in DMF (10 ml), and TEA (0.66 ml, 4.7 mmol) and DCC (1.16 g, 5.64 mmol) were added under ice cooling, followed by stirring overnight at room temperature. After filtering and concentrating, the reaction mixture was redissolved in ethyl acetate and washed sequentially with 10% citric acid, 4% $NaHCO_3$ and aqueous saturated sodium chloride. After drying over anhydrous $MgSO_4$ and concentrating, purification was effected by flash silica gel chromatography (1% MeOH/$CHCl_3$) to yield 1.76 g (89%) of the titled compound as an oily material.

Rf=0.32 ($CHCl_3$/MeOH=49/1)

Step 12-4 Boc-D-Tyr(Me)-L-Ile-D-Pro-OBzl

The compound Boc-L-Ile-D-Pro-OBzl (967 mg, 2.31 mmol) obtained in step 12-3 was dissolved in dioxane (12 ml) and 4N HCl/dioxane (12 ml) was added and the mixture was allowed to stand at room temperature for 1.5 hours. The reaction mixture was concentrated and diethyl ether/petroleum ether (1/3) was added to the residue followed by decantation to yield H-L-Ile-D-Pro-OBzl (745 mg, 91%).

This product was dissolved in DMF (10 ml) and Boc-D-Tyr(Me)-OH (620 mg, 2.10 mmol) and HOBt $H_2O$ (322 mg, 2.10 mmol) were added. Further, TEA (0.63 ml, 4.53 mmol) and BOP (1.05 g, 2.36 mmol) were added under ice cooling, followed by stirring for 2 hours. After being concentrated, the reaction mixture was redissolved in ethyl acetate and washed sequentially with 10% citric acid, 4% $NaHCO_3$ and aqueous saturated sodium chloride. After drying over anhydrous $MgSO_4$ and concentrating, a crude peptide was purified by flash silica gel chromatography (1% MeOH/$CHCl_3$) to yield 881 mg (72%) of the titled compound as an oily material.

HPLC: Rt=21.87 min (column: Wako Pak C18, 4.6×150 mm, 37–100% linear gradient $CH_3CN$/0.1% TFA over 30 min, flow rate 1.0 ml/min)

Step 12-5 Boc-D-Tyr(Me)-L-Ile-D-Pro-OH

The compound Boc-D-Tyr(Me)-L-Ile-D-Pro-OBzl (881 mg, 1.44 mmol) obtained in step 12-4 was dissolved in MeOH (5 ml) and stirred under hydrogen atmosphere overnight using 5% Pd/C (70 mg). The reaction mixture was filtered and concentrated to yield the titled compound.

Rf=0.69 ($CHCl_3$/MeOH/acetic acid=90/10/2)

Step 12-6 Boc-D-Tyr(Me)-L-Ile-D-Pro-L-Glu(Gly-OBzl)-OAll

The compound Boc-L-Glu(Gly-OBzl)-OAll (200 mg, 0.46 mmol) obtained in step 12-2 was dissolved in dioxane (3 ml) and 4N HCl/dioxane (3 ml) was added and the mixture was allowed to stand at room temperature for 1.5 hours. The reaction mixture was concentrated and diethyl ether/petroleum ether (1/3) was added to the residue, followed by decantation to yield H-L-Glu(Gly-OBzl)-OAll HCl (171 mg, quant).

This product was dissolved in DMF (5 ml) and Boc-D-Tyr(Me)-L-Ile-D-Pro-OH (233 mg, 0.46 mmol) and HOBT $H_2O$ (70 mg, 0.46 mmol) were added. Further, TEA (0.17 ml, 1.20 mmol) and BOP (305 mg, 0.69 mmol) were added under ice cooling, followed by stirring overnight. After concentrating, the reaction mixture was redissolved in ethyl acetate and washed sequentially with 10% citric acid, 4% $NaHCO_3$ and aqueous saturated sodium chloride. After drying over anhydrous MgSO$_4$ and concentrating, a crude peptide was purified by flash silica gel chromatography (2% MeOH/CHCl$_3$) to yield 300 mg (79%) of the titled compound as an oily material.

HPLC: Rt=20.99 min (column: Wako Pak C18, 4.6×150 mm, 37–100% linear gradient CH$_3$CN/0.1% TFA over 30 min, flow rate 1.0 ml/min)

FAB-MS: m/z=822 (M+H)$^+$

Step 12-7 cyclo(-L-Glu(Gly-NHOH)-D-Tyr(Me)-L-Ile-D-Pro-)Boc-D-Tyr(Me)-L-Ile-D-Pro-L-Glu(Gly-OBzl)-OAll (300 mg, 0.37 mmol) obtained in step 12-6 was dissolved in CHCl$_3$/acetic acid/N-methylmorpholine (37/2/1) (11 ml) and the environment in the reaction vessel was replaced with Ar gas. Pd(O)(PPh$_3$)$^4$ (1.27 g, 1.1 mmol) was added and the mixture was stirred overnight under Ar atmosphere. After concentrating, the reaction mixture was redissolved in ethyl acetate and washed sequentially with 10% citric acid and saturated aqueous sodium chloride solution. After drying over anhydrous MgSO$_4$, concentration was effected to yield Boc-D-Tyr(Me)-L-Ile-D-Pro-L-Glu(Gly-OBzl)-OH. (300 mg, 0.37 mmol) obtained in step 12-6 was dissolved in CHCl$_3$/acetic acid/N-methylmorpholine (37/2/1) (11 ml) and the environment in the reaction vessel was replaced with Ar gas. Pd(O) (PPh$_3$)$^4$ (1.27 g, 1.1 mmol) was added and the mixture was stirred overnight under Ar atmosphere. After concentrating, the reaction mixture was redissolved in ethyl acetate and washed sequentially with 10% citric acid and saturated aqueous sodium chloride solution. After drying over anhydrous MgSO$_4$, concentration was effected to yield Boc-D-Tyr(Me)-L-Ile-D-Pro-L-Glu(Gly-OBzl)-OH.

Subsequently, by applying the procedure consisting of steps 1-4 to 1-7 of Example 1 (HDA-5), deprotection, cyclization and conversion of the side chain carboxylic acid into hydroxamic acid structure (hydroxyaminocarbonyl structure) were carried out to yield the titled cyclic tetrapeptide.

HPLC: Rt=1555 min (column: Wako Pak C18, 4.6×150 mm, 10–100% linear gradient CH$_3$CN/0.1% TFA over 30 min, flow rate 1.0 ml/min)

FAB-MS: m/z=589 (M+H)$^+$

EXAMPLE 13

HDA-35; cyclo(-L-Glu(b-Ala-NHOH)-D-Tyr(Me)-L-Ile-D-Pro-)

To synthesize the titled cyclic tetrapeptide HDA-35; cyclo (-L-Glu(b-Ala-NHOH)-D-Tyr(Me)-L-Ile-D-Pro-) represented by the following formula (XXII);

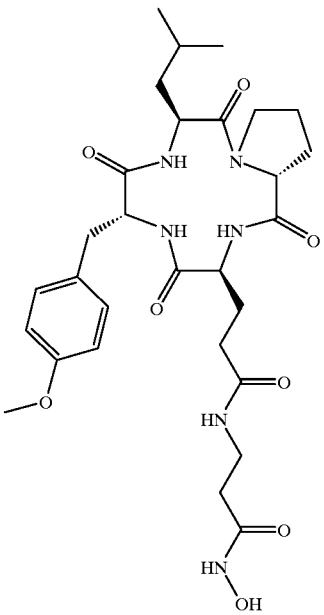

(XXII)

The procedure described in step 12-2 of Example 12 was applied to prepared Boc-L-Glu(b-Ala-OBzl)-Oall and then the procedure consisting of steps 12-3 to 12-7 was applied to yield said cyclic tetrapeptide.

HPLC: Rt=15.28 min (column: Wako Pak C18, 4.6×150 mm, 10–100% linear gradient CH$_3$CN/0.1 % TFA over 30 min flow rate1.0 ml/min)

FAB-MS: m/z=603 (M+H)$^+$

Reference Example 2

Synthesis of HAD-7; cyclo (-L-Lys(Ac)L-Phe-L-Phe-D-Pro-)$_2$

The titled cyclic octapeptide HDA-7 in which the same amino acid sequence as in HDA-6 Of Example 10 is repeated was obtained from Boc-L-Lys(Z)-L-Phe-L-Phe-D-Pro-OtBu obtained by an intermediate step in step 10-1 of Example 10 (HDA-6) corresponding to step 1-3 of Example 1, said intermediate product being subsequently treated by a similar procedure.

HPLC: Rt=16.10 min (column: MS GEL C18, 4.6×150 mm, 10–100% linear gradient CH$_3$CN/0.1% TFA over 30 min, flow rate 1.0 ml/min)

FAB-MS: m/z=1124 (M+H)$^+$

Reference Example 3

Synthesis of HDA-14; cyclo(-L-Asu(NHOH)-D-Tyr(Me)-L-Ile-L-Pro-)$_2$

The titled cyclic octapeptide RDA-14 in which the same amino acid sequence as in HDA-30 of Example 18 to be mentioned below is repeated was obtained through preparation of Boc-L-Asu(NHOH)-D-Tyr(Me)-L-Ile-L-Pro-OtBu by applying the procedure of Example 1 (HDA-5).

HPLC: Rt=20.59 min (column: Wako Pak C18, 4.6×150 mm, 10–100% linear gradient CH$_3$CN/0.1% TFA over 30 min, flow rate 1.0 ml/min)

FAB-MS: m/z=1170 (M+Na)$^+$

EXAMPLE 14

HDA-38: cyclo(L-Asu(NHOH)-D-Phe-L-Phe-L-Pro-)

The process for the synthesis of the cyclic tetrapeptide HDA-38; cyclo(-L-Asu(NHOH)-D-Phe-L-Phe-L-Pro-) represented by the following formula (XXIII):

(XXIII)

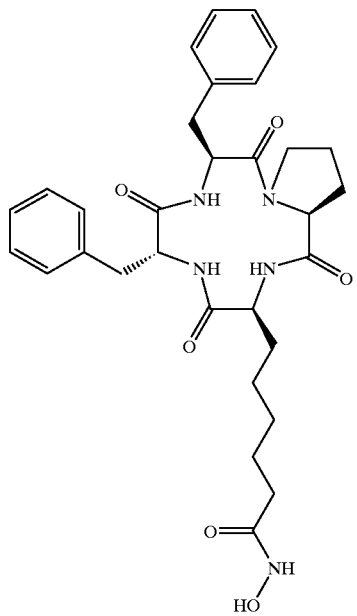

will be briefly described.

Step 14-1 cyclo(-L-Asu(OBzl)-D-Phe-L-Phe-L-Pro-)

Boc-L-Asu(OBzl)-OH (380 mg, 1.0 mmol) and an oxime resin (OxR 1.0 g) were condensed using DCC (206 mg, 1.0 mmol) in DCM (15 ml). Introduction rate: 0.47 mmol/g resin. Using 1 g of this resin, Boc-L-Pro-OH, Boc-L-Phe-OH and Boc-D-Phe-OH were sequentially condensed in a conventional manner for solid phase synthesis by Boc-strategy to yield Boc-D-Phe-L-Phe-L-Pro-L-Asu(OBzl)-OxR. Then, after removal of Boc, 2 equivalent amounts each of acetic acid (57 ml, 1.0 mmol) and DIEA (0.15 ml, 1.0 mmol) were added to a DMF (15 ml) suspension and the reaction vessel was shaken for 20 hours. The reaction mixture was filtered and concentrated, and water was added to the residue to solidify it. Thus, 110 mg (38%) of the titled cyclic tetrapeptide compound was obtained as a white powdery material.

HPLC: Rt=15.72 min (column: Wako Pak C4, 4.6×150 mm, 37–100% linear gradient $CH_3CN$/0.1% TFA over 30 min)

Step 14-2 cyclo(-L-Asu(NHOH)-D-Phe-L-Phe-L-Pro-)

Subsequently, catalytic reduction in DMF and subsequent condensation with hydroxylamine were effected in a similar procedure to steps 1-6 and 1-7 in the preparation process of Example 1 (HDA-5). The reaction mixture was concentrated, dissolved in DMSO, preparatively purified by reverse-phase HPLC (column: YMC-Pack ODS A-323, 10×250 mm, 36% $CH_3CN$/0.1% TFA), and lyophilized to yield 9 mg (10%) of the titled compound.

HPLC: Rt=16.94 min (column: MS GEL C18, 4.6×150 mm, 10–100% linear gradient $CH_3CN$/0.1% TFA over 30 min)

FAB-MS: m/z=578 (M+H)hu +

EXAMPLE 15

HDA-37; cyclo(-L-Asu(NHOH)-D-Pro-L-Phe-D-Phe-)

The cyclic tetrapeptide HDA-37; cyclo(-L-Asu(NHOH)-D-Pro-L-Phe-D-Phe-) represented by the following formula (XXIV):

(XXIV)

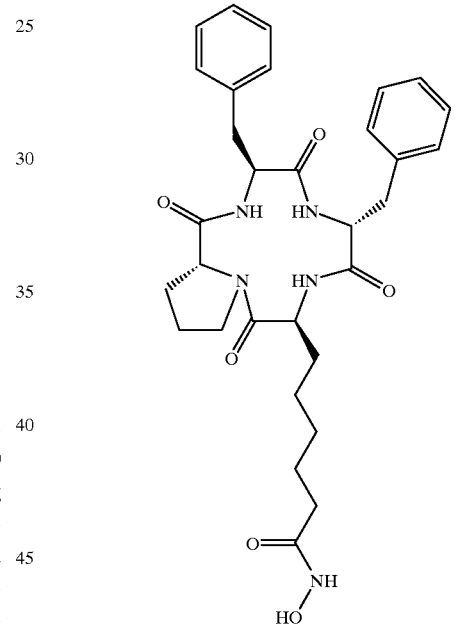

was synthesized starting from Boc-L-Phe-OxR according to the procedure described in Example 14.

HPLC: rt=17.65 min (column: MS GEL C18, 4.6×150 mm, 10–100% linear gradient $CH_3CN$/0.1% TFA over 30 min, flow rate 1.0 ml/min)

FAB-MS: m/z=578 $(M+H)^+$

EXAMPLE 16

HDA-19; cyclo(-L-Asu(NHOH)-L-Phe-D-Phe-L-Pro-)

The cyclic tetrapeptide HDA-39; cyclo(-L-Asu(NHOH)-L-Phe-D-Phe-L-Pro-) represented by the following formula (XXV):

(XXV)

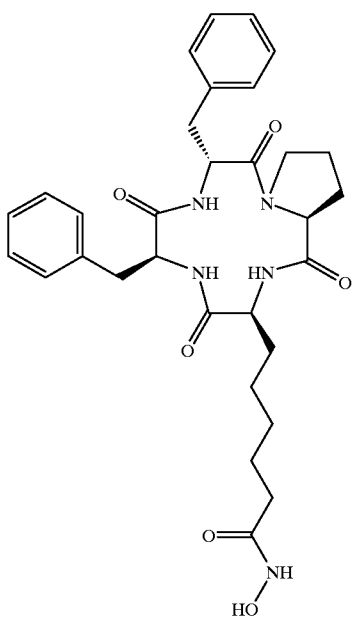

was synthesized starting from Boc-L-Asu(OBzl)-OxR according to the procedure described in Example 14.

HPLC: Rt=16.16 min (column: Wako Pak C18, 4.6×150 mm, 10–100% linear gradient $CH_3CN$/0.1% TFA over 30 min, flow rate 1.0 ml/min)

FAB-MS: m/z=578 (M+H)$^+$

EXAMPLE 17

HDA-40; cyclo(-L-Asu(NHOH)-L-Phe-L-Phe-Sar-)

The cyclic tetrapeptide HDA-40; cyclo(-L-Asu(NHOH)-L-Phe-L-Phe-Sar-) represented by the following formula (XXVI):

(XXVI)

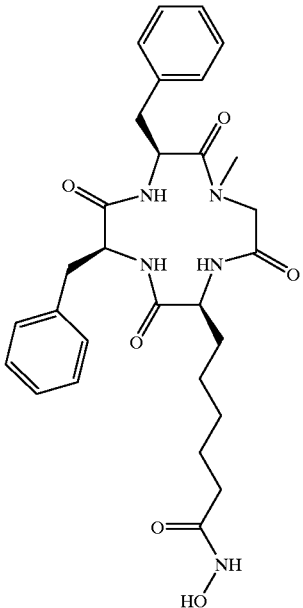

was synthesized starting from Boc-L-Asu(OBzl)-OxR according to the procedures described in Example 14.

HPLC: Rt=15.86 min (column: Wako Pak C18, 4.6×150 mm, 10–100% linear gradient $CH_3CN$/0.1% TFA over 30 min, flow rate 1.0 ml/min)

FAB-MS: m/z=552 (M+H)$^+$

EXAMPLE 18

HDA-30; cyclo(-L-Asu(NHOH)-D-Tyr(Me)-L-Ile-L-Pro-)

The process for the synthesis of the cyclic tetrapeptide HDA-30; cyclo(-L-Asu(NHOH)-D-Tyr(Me)-L-Ile-L-Pro-) represented by the following formula (XXVII):

(XXVII)

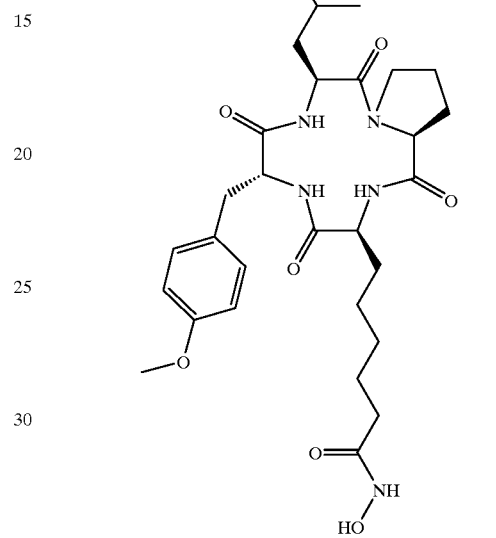

will be briefly described.

Step 18-1 Boc-L-Ile-L-Pro-L-Asu(OBzl)-D-Tyr(Me)-OH

Boc-L-Tyr(Me)-OH (591mg, 2.0mmol) and an oxime resin (OxR, 2.0 g) were condensed using DCC (412 mg, 2.0 mmol) in toluene (30 ml). Introduction rate: 0.36 mmol/g resin. Using 1 g of this resin, Boc-L-Asu(OBzl)-OH, Boc-L-Pro-OH and Boc-L-Ile-OH were sequentially condensed in a conventional manner for solid phase synthesis by Poc-strategy to yield Boc-L-Ile-L-Pro-L-Asu(OBzl)-D-Tyr(Me)-OxR. Then, 1-hydroxypiperidine (182 mg, 1.80 mmol) was added to a suspension in DMF (15 ml) and the reaction vessel was shaken for 24 hours. The reaction mixture was filtered, concentrated, and dissolved in acetic acid (7 ml) and $Na_2S_2O_4$ (312 mg, 1.80 mmol) was added, followed by stirring for 1 hour. After concentrating, the reaction mixture was redissolved in ethyl acetate and washed with sequentially with 10% citric acid and aqueous saturated sodium chloride. Drying over anhydrous $MgSO_4$ and concentrating yielded 368 mg (quant) of the titled chained tetrapeptide compound as an oily material.

HPLC: Rt=17.45 min (column: Wako Pak C4, 4.6×150 mm, 37–100% linear gradient $CH_3CN$/0.1% TFA over 30 min)

Step 18-2 H-L-Ile-L-Pro-L-Asu(OBzl)-D-Tyr(Me)-OH TFA

To the compound Boc-L-Ile-L-Pro-L-Asu(OBzl)-D-Tyr(Me)-OH (368 mg, 0.48 mmol) obtained in step 18-1, TFA (3 ml) was added under ice cooling and the mixture was allowed to stand for 30 minutes. The reaction mixture was concentrated and diethyl ether/petroleum ether was added to the residue to solidify it. Thus, 338 mg (90%) of the titled compound was obtained as a white powdery material.

Step 18-3 cyclo(-L-Asu(NHOH)-D-Tyr(Me)-L-Ile-L-Pro-)

Subsequently, by applying the procedure consisting of steps 1-5 to 1-7 of Example 1 (HDA-5), cyclization and conversion of the side chain carboxylic acid into hydroxamic acid structure (hydroxyaminocarbonyl structure) were carried out to yield the titled cyclic tetrapeptide.

HPLC: Rt=17.18 min (column: Wako Pak C18, 4.6×150 mm, 10–100% linear gradient $CH_3CN$/0.1% TFA over 30 min, flow rate 1.0 ml/min)

FAB-MS: m/z=574 $(M+H)^+$

EXAMPLE 19

HDA-28; cyclo(-L-Asu(NHOH)-D-Phe-L-Leu-L-Pro-)

The cyclic tetrapeptide HDA-28; cyclo(-L-Asu(NHOH)-D-Phe-L-Leu-L-Pro-) represented by the following formula (XXVIII):

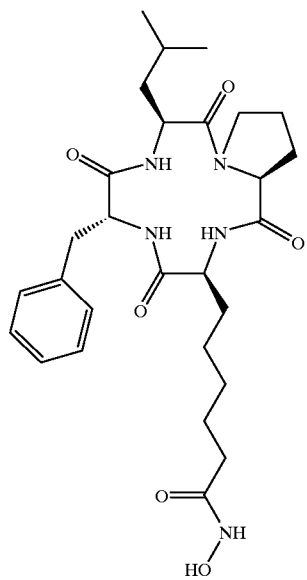

(XXVIII)

was synthesized starting from Boc-D-Phe-OxR according to the procedure described in Example 18.

HPLC: Rt=17.50 min (column: Wako Pak C18, 4.6×150 mm, 10–100% linear gradient $CH_3CN$/0.1% TFA over 30 min, flow rate 1.0 ml/min)

FAB-MS: m/z=544 $(M+H)^+$

EXAMPLE 20

HDA-27; cyclo(-L-Asu(NHOH)-D-Phe-L-Phe-D-Pro-)

The cyclic tetrapeptide HDA-27; cyclo(-L-Asu(NHOH)-D-Phe-L-Phe-D-Pro-) represented by the following formula (XXIX):

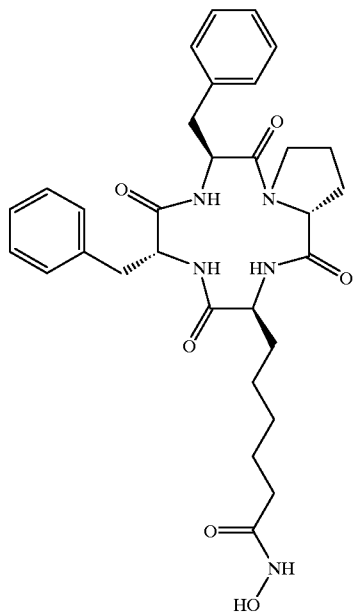

(XXIX)

was synthesized starting from Boc-D-Phe-OxR according to the procedure described in Example 18.

HPLC: Rt=19.35 min (column: Wako Pak C18, 4.6×150 mm, 10–100% linear gradient $CH_3CN$/0.1% TFA over 30 min, flow rate 1.0 ml/min)

FAB-MS: m/z=578 $(M+H)^+$

EXAMPLE 21

HDA-31; cyclo(-L-Asu(NHOH)-D-Tyr(Me)-L-Ile-D-Pro-)

The cyclic tetrapeptide HDA-31; cyclo(-L-Asu(NHOH)-D-Tyr(Me)-L-Ile-D-Pro-) represented by the following formula (XXX):

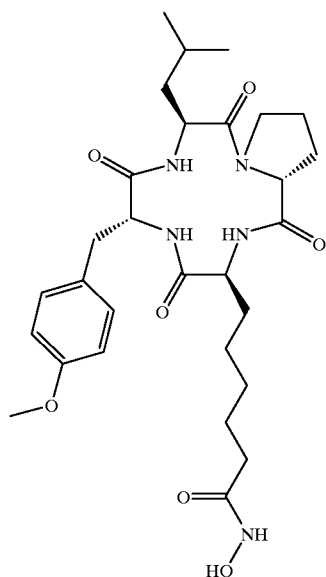

(XXX)

was synthesized starting from Boc-D-Tyr(Me)-OxR according to the procedure described in Example 18.

HPLC: Rt=18.63 min (column: Wako Pak C18, 4.6×150 mm, 10–100% linear gradient CH₃CN/0.1% TFA over 30 min, flow rate 1.0 ml/min)

FAB-MS: m/z=574 (M+H)$^+$

EXAMPLE 22

HDA-29; cyclo(-L-Asu(NHOH)-D-PheL-Leu-D-Pro-)

The cyclic tetrapeptide HDA-29; cyclo(-L-Asu(NHOH)-D-Phe-L-Leu-D-Pro-) represented by the following formula (XXXI):

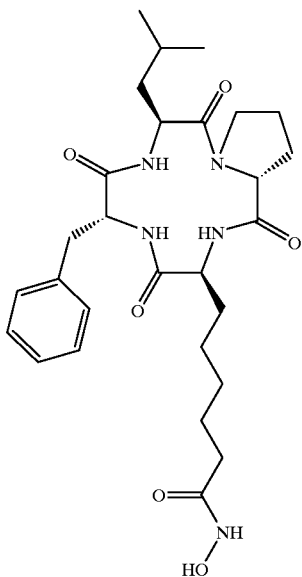

(XXXI)

was synthesized starting from Boc-D-Phe-OxR according to the procedure described in Example 18.

HPLC: Rt=17.88 min (column: Wako Pak C18, 4.6×150 mm, 10–100% linear gradient CH₃CN/0.1% TFA over 30 min, flow rate 1.0 m/min)

FAB-MS: m/z=544 (M+H)$^+$

EXAMPLE 23

HDA-30; cyclo(-L-A//(NHOH)-D-Tyr(Me)-L-Ile-L-Pro-)

An alternative process for the synthesis of the cyclic tetrapeptide HDA-30; cyclo(-L-Asu(NHOH)-D-Tyr(Me)-L-Ile-L-Pro-) represented by the following formula (XXVII):

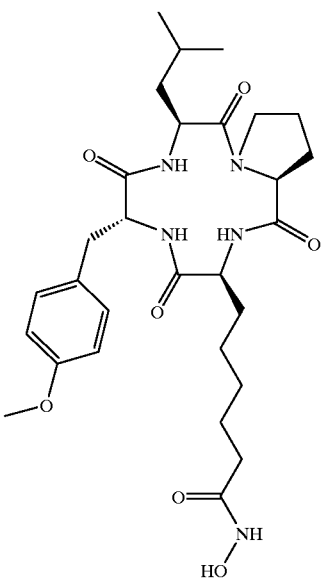

(XXVII)

will be briefly described.

Step 23-1 Boc-L-Asu(OBzl)-OTMe

To a solution of Boc-L-Asu(OBzl)-OH (2.38 g, 6.27 mmol) and trimethylsilylethanol (1.79 ml, 12.53 mol) in DCM (12 ml), 4-dimethylaminopyridine (76 mg, 0.63 mmol) and DCC (1.55 g, 7.52 mmol) were added under ice cooling followed by stirring overnight. The reaction mixture was filtered, concentrated, redissolved in ethyl acetate and washed sequentially with 10% citric acid, 4% NaHCO₃ and aqueous saturated sodium chloride. After drying over anhydrous MgSO₄ and concentrating, the residue was purified by flash silica gel chromatography (ethyl acetate/hexane=1/4) to yield 3.18 g (quant) of the titled compound as an oily material.

Rf=0.50 (ethyl acetate/hexane=1/4)

Step 23-2 Boc-L-Asu-OTme

The compound Boc-L-Asu(OBzl)-OTme (1.55 g, 3.13 mmol) obtained in step 23-1 was dissolved in THF (6 ml) and stirred under hydrogen atmosphere for 3 hours in the presence of 5% Pd/C (200 mg). The reaction mixture was filtered and concentrated to yield 1.41 g (quant) of the titled compound as an oily material.

Rf=0.38 (CHCl₃/MeOH/acetic acid=19/1/0.2)

Step 23-3 cyclo(-L-Asu(NHOH)-D-Tyr(Me)-L-Ile-L-Pro-)

Boc-L-Asu-OTme (1.30 g, 3.32 mmol) obtained in step 23-2 and an oxime resin (3.32 g) were condensed using DCC (685 mg, 3.32 mmol) in DCM (50 ml) to yield Boc-L-Asu (OxR)-OTme. Introduction rate: 0.38 mmol/g resin. Using 350 mg (0.13 mmol) of this resin, Boc-L-Pro-OH, Boc-L-Ile-OH and Boc-D-Tyr(Me)-OH were sequentially condensed in a conventional manner for solid phase synthesis by Boc-strategy to yield Boc-D-Tyr(Me)-L-Ile-L-Pro-L-Asu (OxR)-OTme.

Then, 400 mg of the peptide carrying resin was suspended in DMF (6 ml) and a THF solution (0.76 ml) of 1M tetrabutylammonium fluoride was added with a syringe, followed by shaking at room temperature for 30 minutes to remove Tme groups. Further, Boc groups were removed in DCM. After resuspension in DMF (6 ml), BOP (176 mg, 0.39 mmol), HOBt H₂O (82 mg, 0.52 mmol) and DIEA (93 ml, 0.52 mmol) were added and cyclizing reaction was carried out for 2 hours on the resin. After washing with DMF, cyclo(-D-Tyr(Me)-L-Ile-L-Pro-L-Asu(OxR)-) was suspended in DMF (6 ml). Hydroxylamine hydrochloride (46 mg, 0.65 mmol), DIEA (0.12 ml, 0.65 mmol) and acetic acid (40 ml, 0.65 mmol) were added and the mixture was shaken overnight to eliminate cyclic tetrapeptide hydroxamic acid. The reaction mixture was filtered, concentrated, dissolved in DMF, preparatively purified by reverse-phase HPLC (column: YMC-Pack ODS A-323, 10×250 mm, 32% CH₃CN/0.1% TFA), and lyophilized to yield 37 mg (50%) of the titled compound.

HPLC: Rt=17.18 min (column: Wako Pak C18, 4.6×150 mm, 10–100% linear gradient CH₃CN/0.1% TFA over 30 min, flow rate 1.0 ml/min)

FAB-MS: m/z=574 (M+H)⁺

EXAMPLE 24

HDA-49; cyclo(-L-Asu(NHOH)-D-Tyr(Me)-L-Ile-L-Pip-)

The process for the synthesis of the titled cyclic tetrapeptide HDA-49 represented by the following formula (XXXII):

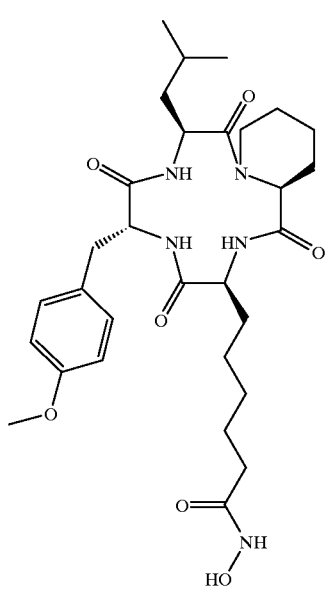

(XXXII)

will be briefly described.

Starting from Boc-D-Tyr(Me)-OxR, Boc-L-Ile-L-Pip-L-Asu(OBzl)-D-Tyr(Me)-OxR was prepared in a conventional manner for solid phase synthesis. However, double coupling using HATU was done for the condensation of Boc-L-Ile-OH. Subsequently, cyclization and conversion of the side chain carboxylic acid to hydroxamic acid structure were carried out according to the procedure of Example 18 for HDA-30; cyclo(-L-Asu(NHOH)-D-Tyr(Me)-L-Ile-L-Pro-).

HPLC: Rt=17.94 min (column: Wako Pak C18, 4.6×150 mm, 10–100% linear gradient CH3CN/0.1% TFA over 30 min, flow rate 1.0 ml/min)

FAB-MS: m/z=588 (M+H)⁺

EXAMPLE 25

HDA-50; cyclo(-L-Asu(NHOH)-D-Tyr(Me)-L-Ile-D-Pip-)

The process for the synthesis of the titled cyclic tetrapeptide HDA-50 represented by the following formula (XXXIII):

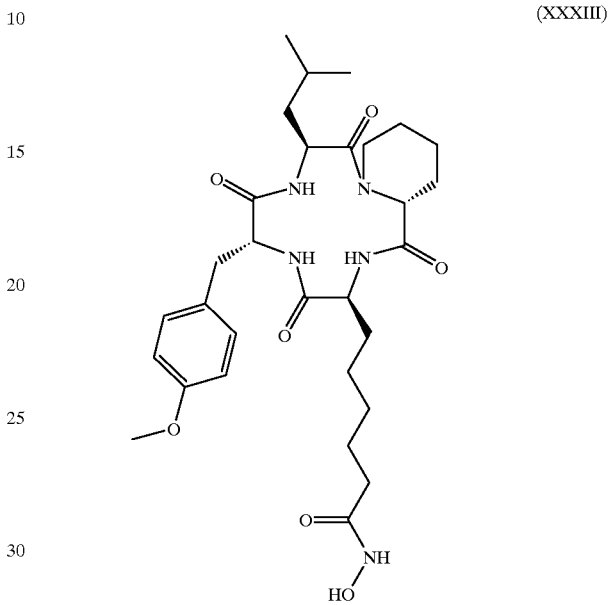

(XXXIII)

will be briefly described.

Starting from Boc-D-Tyr(Me)-OxR, Boc-L-Ile-D-Pip-L-Asu(OBzl)-D-Tyr(Me)-OxR was prepared in a conventional manner for solid phase synthesis. However, double coupling using HATU was done for the condensation of Boc-L-Ile-OH. Subsequently, cyclization and conversion of the side chain carboxylic acid to hydroxamic acid structure were carried out according to the procedure of Example 18 for HDA-30; cyclo(-L-Asu(NHOH)-D-Tyr(Me)-L-Ile-L-Pro-) to yield the titled cyclic tetrapeptide HDA-50.

HPLC: Rt=20.15 min (column: Wako Pak C18, 4.6×150 mm, 10–100% linear gradient CH₃CN/0.1% TFA over 30 min, flow rate 1.0 ml/min)

FAB-MS: m/z=588 (M+H)⁺

EXAMPLE 26

HDA-51; cyclo(-L-Asu(NHOH)-D-Tyr(Me)-L-Ile-L-Tic-)

(Tic: 1,2,3,4-tetrahydroisoquinoline-3-carboxylic acid)

The process for the synthesis of the titled cyclic tetrapeptide HDA-51 represented by the following formula (XXXIV):

(XXXIV)

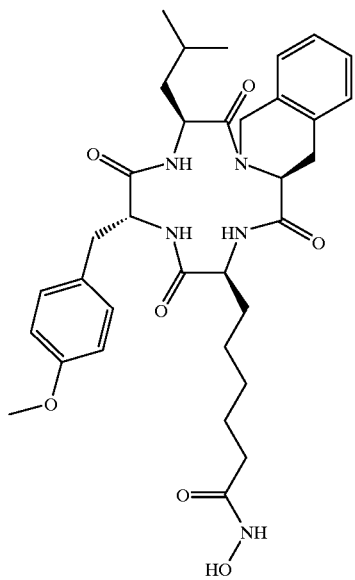

(XXXV)

will be briefly described.

Starting from Boc-D-Tyr(Me)-OxR, Boc-L-Ile-L-Tic-L-Asu(OBzl)-D-Tyr(Me)-OxR was prepared in a conventional manner for solid phase synthesis. However, double coupling using HATU was done for the condensation of Boc-L-Ile-OH. Subsequently, cyclization and conversion of the side chain carboxylic acid to hydroxamic acid structure were carried out according to the procedure of Example 18 for HDA-30; cyclo(-L-Asu(NHOH)-D-Tyr(Me)-L-Ile-L-Pro-) to yield the titled cyclic tetrapeptide HDA-51.

HPLC: Rt=18.48 min (column: Wako Pak C18, 4.6×150 mm, 10–100% linear gradient $CH_3CN$/0.1% TFA over 30 min, flow rate 1.0 ml/min)

FAB-MS: m/z=636 $(M+H)^+$

EXAMPLE 27

HDA-52; cyclo(-L-Asu(NHOH)-D-Tyr(Me)-L-Ile-D-Tic-)

The process for the synthesis of the titled cyclic tetrapeptide HDA-52 represented by the following formula (XXXV):

will be briefly described.

Starting from Boc-D-Tyr(Me)-OxR, Boc-L-Ile-D-Tic-L-Asu(OBzl)-D-Tyr(Me)-OxR was prepared in a conventional manner for solid phase synthesis. However, double coupling using HATU was done for the condensation of Boc-L-Ile-OH. Subsequently, cyclization and conversion of the side chain carboxylic acid to hydroxamic acid structure were carried out according to the procedure of Example 18 for HDA-30; cyclo(-L-Asu(NHOH)-D-Tyr(Me)-L-Ile-L-Pro-) to yield the titled cyclic tetrapeptide HDA-52.

HPLC: Rt=20.78 min (column: Wako Pak C18, 4.6×150 mm, 10–100% linear gradient $CH_3CN$/0.1% TFA over 30 min, flow rate 1.0 ml/min)

FAB-MS: m/z=636 $(M+H)^+$

EXAMPLE 28

HDA-53; cyclo(-L-Asu(NHOH)-D-Phe-L-Leu-L-Pip-)

The process for the synthesis of the titled cyclic tetrapeptide HDA-53 represented by the following formula (XXXVI):

(XXXVI)

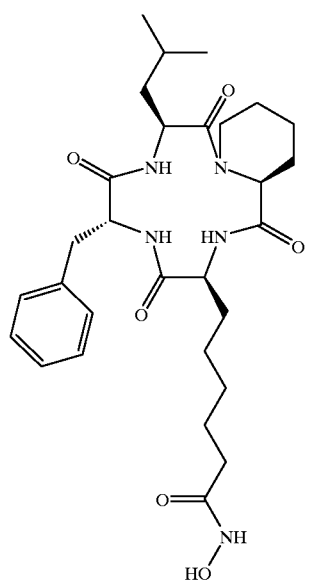

will be briefly described.

Starting from Boc-D-Phe-OxR, Boc-L-Leu-L-Pip-L-Asu(OBzl)-D-Phe-OxR was prepared in a conventional manner for solid phase synthesis. However, double coupling using HATU was done for the condensation of Boc-L-Leu-OH. Subsequently, cyclization and conversion of the side chain carboxylic acid to hydroxamic acid structure were carried out according to the procedure of Example 18 for HDA-30; cyclo(-L-Asu(NHOH)-D-Tyr(Me)-L-Ile-L-Pro-) to yield the titled cyclic tetrapeptide HDA-53.

HPLC: Rt=18.26 min (column: Wako Pak C18, 4.6×150 mm, 10–100% linear gradient CH$_3$CN/0.1% TFA over 30 min, flow rate 1.0 ml/min)

FAB-MS: m/z=558 (M+H)$^+$

EXAMPLE 29

HDA-42; cyclo(-L-Api(NHOH)-D-Tyr(Me)-L-Ile-D-Pro-)

The process for the synthesis of the titled cyclic tetrapeptide HDA-42 represented by the following formula (XXXVII):

(XXXVII)

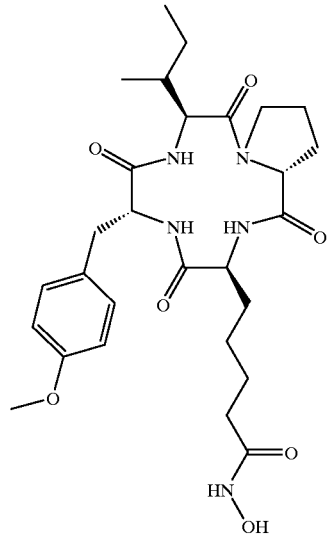

will be briefly described.

Starting from Boc-L-Api(OBzl)-OxR, cyclization and conversion of the side chain carboxylic acid to hydroxamic acid structure were carried out according to the procedure of Example 14 for HDA-38; cyclo(-L-Asu(NHOH)-D-Phe-L-Phe-L-Pro-) to yield the titled cyclic tetrapeptide HDA-42.

HPLC: Rt=17.67 min (column: Wako Pak C18, 4.6×150 mm, 10–100% linear gradient CH$_3$CN/0.1% TFA over 30 min, flow rate 1.0 ml/min)

FAB-MS: m/z=560 (M+H)$^+$

EXAMPLE 30

HDA-43; cyclo(-L-Aaz(NHOH)-D-Tyr(Me)-L-Ile-D-Pro-)

The process for the synthesis of the titled cyclic tetrapeptide HDA-43 represented by the following formula (XXXVIII):

(XXXVIII)

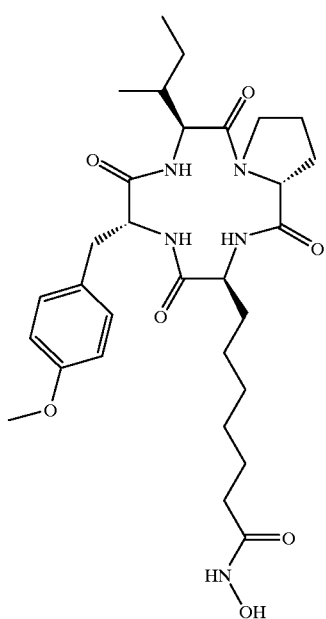

will be briefly described.

Starting from Boc-L-Aaz(OBzl)-OxR, cyclization and conversion of the side chain carboxylic acid to hydroxamic acid structure were tarried out according to the procedure of Example 14 for HDA-38; cyclo(-L-Asu(NHOH)-D-Phe-L-Phe-L-Pro-) to yield the titled cyclic tetrapeptide HDA-43.

HPLC: Rt=18.92 min (column: Wako Pak C18, 4.6×150 mm, 10–100% linear gradient $CH_3CN$/0.1% TFA over 30 min, flow rate 1.0 ml/min)

FAB-MS: m/z=588 $(M+H)^+$

EXAMPLE 31

HDA-44; cyclo(-L-Asu(NHOH)-D-Tyr(Me)-L-Ala-D-Pro-)

The process for the synthesis of the titled cyclic tetrapeptide HDA-44 represented by the following formula (XXXIX):

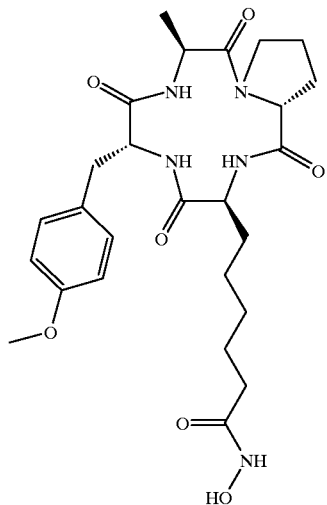
(XXXIX)

will be briefly described.

Starting from Boc-L-Asu(OBzl)-OxR, cyclization and conversion of the side chain carboxylic acid to hydroxamic acid structure were carried out according to the procedure of Example 14 for HDA-38; cyclo(-L-Asu(NHOH)-D-Phe-L-Phe-L-Pro-) to yield the titled cyclic tetrapeptide HDA-44.

HPLC: Rt=12.89 min (column: Wako Pak C18, 4.6×150 mm, 10–100% linear gradient $CH_3CN$/0.1% TFA over 30 min, flow rate 1.0 ml/min)

FAB-MS: m/z=532 $(M+H)^+$

EXAMPLE 32

HDA-45; cyclo(-L-Asu(NHOH)-D-Phe-L-Ala-D-Pro-)

The process for the synthesis of the titled cyclic tetrapeptide HDA-45 represented by the following formula (XXXX):

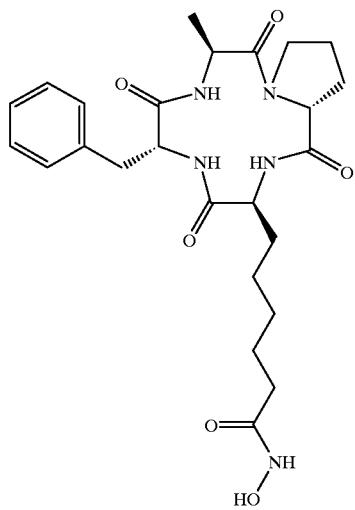
(XXXX)

will be briefly described.

Starting from Boc-L-Asu(OBzl)-OxR, cyclization and conversion of the side chain carboxylic acid to hydroxamic acid structure were carried out according to the procedure of Example 14 for HDA-38; cyclo(-L-Asu(NHOH)-D-Phe-L-Phe-L-Pro-) to yield the titled cyclic tetrapeptide HDA-45.

HPLC: Rt=12.91 min (column: Wako Pak C18, 4.6×150 mm, 10–100% linear gradient $CH_3CN$/0.1% TFA over 30 min, flow rate 1.0 ml/min)

FAB-MS: m/z=544 $(M+H)^+$

EXAMPLE 33

HDA-46; cyclo(-L-Asu(NHOH)-D-Phe-L-Ile-D-Pro-)

The process for the synthesis of the titled cyclic tetrapeptide HDA-46 represented by the following formula (XXXXI):

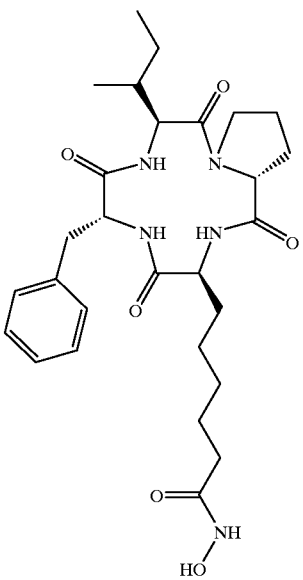
(XXXXI)

will be briefly described.

Starting from Boc-L-Asu(OBzl)-OxR, cyclization and conversion of the side chain. carboxylic acid to hydroxamic acid structure were carried out according to the procedure of Example 14 for HDA-38; cyclo(-L-Asu(NHOH)-D-Phe-L-Phe-L-Pro-) to yield the titled cyclic tetrapeptide HDA-46.

HPLC: Rt=18.46 min (column: Wako Pak C18, 4.6×150 mm, 10–100% linear gradient CH$_3$CN/0.1% TFA over 30 min, flow rate 1.0 ml/min)

FAB-MS; m/z=502 (M+H)$^+$

EXAMPLE 34

Synthesis of HDA-47; cyclo(-L-Asu(NHOH)-D-Naf-L-Ile-D-Pro-) (D-Naf: D-1-naphthylalanine)

The process for the synthesis of the titled cyclic tetrapeptide HDA-47 represented by the following formula (XXXXII):

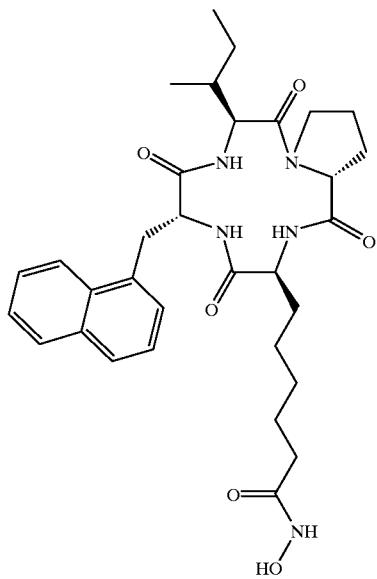

(XXXXII)

will be briefly described.

Starting from Boc-L-Asu(OBzl)-OxR, cyclization and conversion of the side chain carboxylic acid to hydroxamic acid structure were carried out according to the procedure of Example 14 for HDA-38; cyclo(-L-Asu(NHOH)-D-Phe-L-Phe-L-Pro-) to yield the titled cyclic tetrapeptide HDA-47.

HPLC: Rt=20.52 min (column: Wako Pak C18, 4.6×150 mm, 10–100% linear gradient CH$_3$CN/0.1% TFA over 30 min, flow rate 1.0 ml/min)

FAB-MS: m/z=594 (M+H)$^+$

EXAMPLE 35

Synthesis of HDA-48; cyclo(-L-Asu(NHOH)-D-Pya-L-Ile-D-Pro-) (D-Pya: D-1-pyrenylalanine)

The process for the synthesis of the titled cyclic tetrapeptide HDA-48 represented by the following formula (XXXXIII):

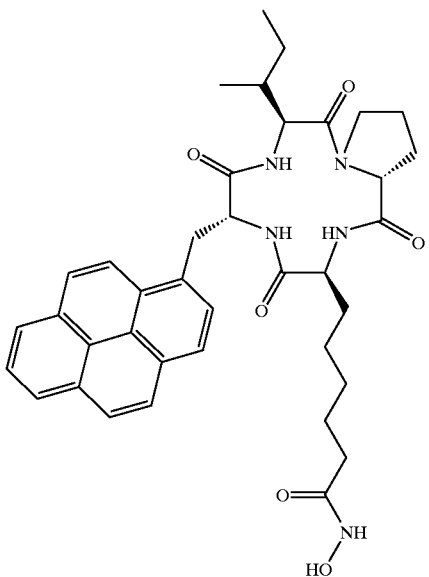

(XXXXIII)

will be briefly described.

Starting from Boc-L-Asu(OBzl)-OXR, cyclization and conversion of the side chain carboxylic acid to hydroxamic acid structure were carried out according to the procedure of Example 14 for HDA-38; cyclo(-L-Asu(NHOH)-D-Phe-L-PheL-Pro-) to yield the titled cyclic tetrapeptide HDA-48.

HPLC: Rt=23.56 min (column: Wako Pak C18, 4.6×150 mm, 10–100% linear gradient CH$_3$CN/0.1% TFA over 30 min, flow rate 1.0 ml/min)

FAB-MS: m/z=667.81 (M+H)$^+$

Test Example 1

MHC class-I molecule expression promoting activity

The cyclic tetrapeptide derivatives of the present invention were investigated for their MHC class-I molecule expression promoting actions in the following test. Thus, in the test, the cyclic tetrapeptide derivatives of the present invention were allowed to act on cancer cells and it was demonstrated that they promoted MHC class-I molecule expression.

Test Method

The cancer cells used were mouse melanoma cells, B16/BL6 cells, provided by, the National Cancer Institute, U.S.A. Said cells were cultivated in MEM media supplemented with 10% FBS at 37° C. in the presence of 5% carbon dioxide in an humidified incubator.

A compound to be tested was preliminarily dissolved in dimethyl sulfoxide (DMSO) and adjusted to a concentration of 100 mM or 10 mM (source solution). A commercially available product, trichostatin A (purchased from Wako Pure Chemical, Japan) which has been proved to have a histone deacetylase enzyme inhibiting activity, was also dissolved in DMSO and adjusted to a concentration of 5 mg/ml (16.54 mM) (source solution). Trichostatin A was used as a positive control compound for MHC class-I molecule expression promoting action due to histone deacetylase enzyme inhibiting activity. DMSO used as a solvent for the source solution of a compound to be tested would inevitably be introduced into the medium in the test; however, it had been separately confirmed not to affect the test results in amounts within the range used in the test.

Said B16/BL6 cells were inoculated on 96 well microplate at a cell density of 5000 cells per well, each well containing 200 μl of said medium. After 24 hours of cultivation, 10 μl of a sample containing a given amount of the source solution of a compound to be tested which had been diluted in the medium was added and cultivated for additional 72 hours. Thereafter, each well was once washed with PBS (phosphate buffered saline) and floating cells and the medium were removed. Then, the well was treated with 0.1% glutaraldehyde solution for 3 minutes to fix the cells.

The amount of MHC class-I molecule expressed on the surface of the fixed cells was measured by the following method. Anti-H-2K$^b$D$^b$D$^d$ antibody, which is an antibody against mouse MHC classI molecule (commercially available from Meiji Milk Co., Ltd), was used as a primary antibody, biotinylated anti-mouse IgG+M (commercially available from Chemicon) was used as a secondary antibody, and streptavidin-β-galactosidase conjugate (commercially available from BRL) was reacted as a labelling enzyme. The amount of the thus labelled enzyme β-galactosidase was measured in a microplate reader by recording the fluorescent intensity (excitation: 365 nm, fluorescence: 450 nm) derived from the enzymaticreaction product using 4-methylumbelliferyl-β-D-galactoside (commercially available from Nacalai Tesque) as a substrate. A fluorescence intensity measured for another well to which no compound to be tested was added and which was treated in a similar way without adding said primary antibody was used as a background level. The value obtained by subtracting said background level from the, actually measured value (an apparent value including the background level) was the true measurement reflecting the amount of expressed MHC class-I molecule.

A group without the addition of any compound to be tested was used as a reference group and the measurement of MHC class-I molecule expressed in said group was used as a standard value. The amount of MHC class-I molecule expressed at a concentration of addition of each test compound is shown as a relative amount, said standard value taken as one (1). For each compound to be tested, various concentrations of addition were selected to investigate the dependency of MHC class-I molecule expression promoting action on the concentration of addition.

Figure 3:
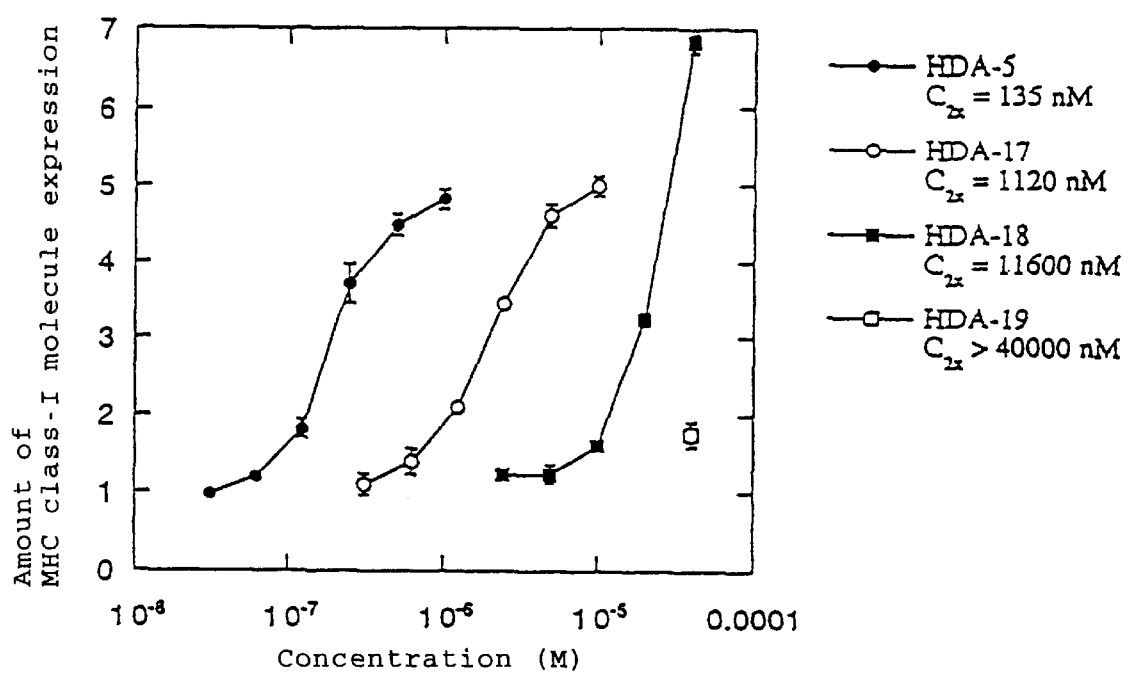
FIG. 3 shows the MHC class-I molecule expression promoting action of the compounds of Examples 1 to 3 and Reference Example 1, as well as their dependence on the concentration of addition.
Figure 4:
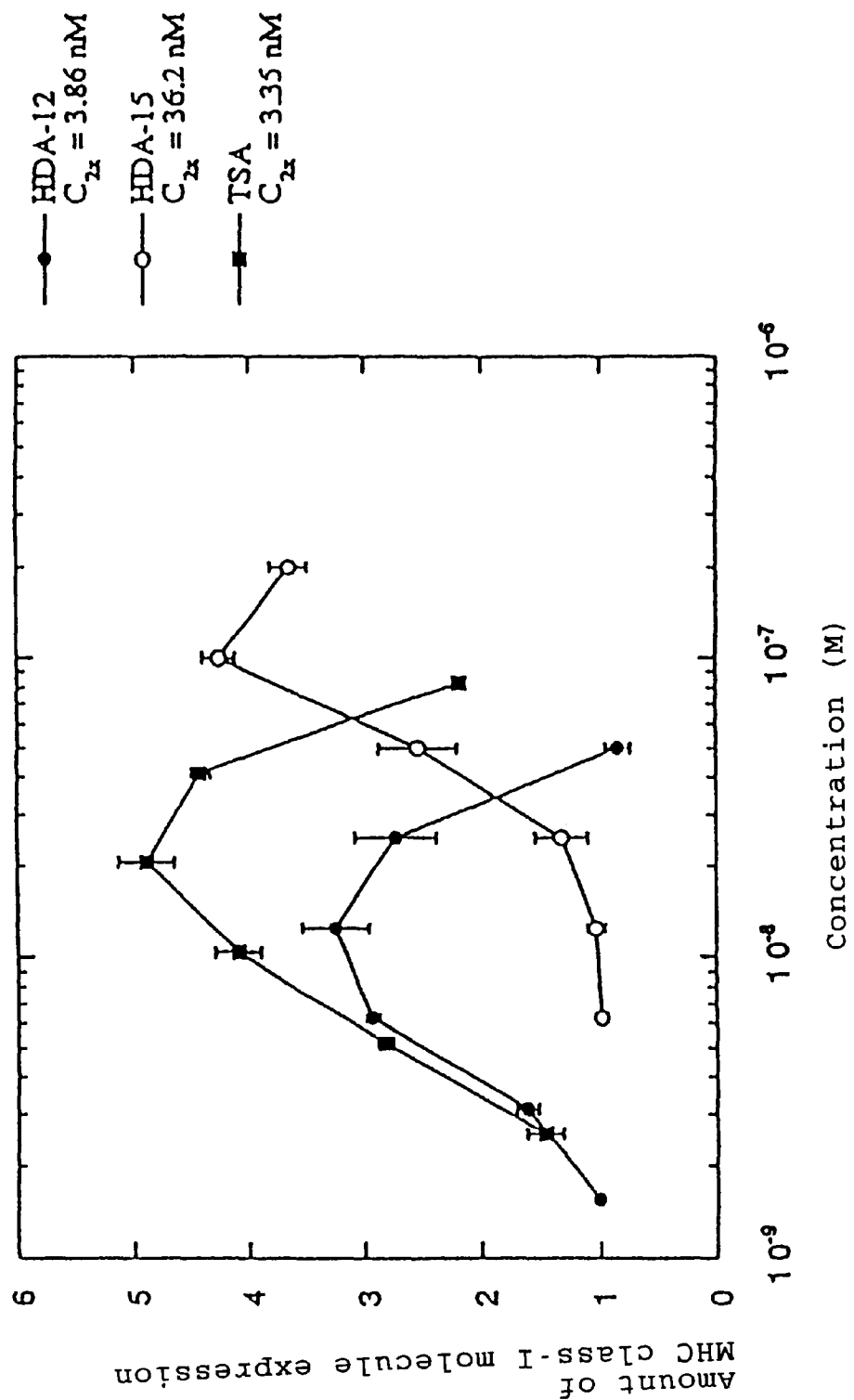
FIG. 4 shows the MHC class-I molecule expression promoting action of the compounds of Examples 4 and 5 and trichostatin A, as well as their dependence on the concentration of addition.
Figure 5:
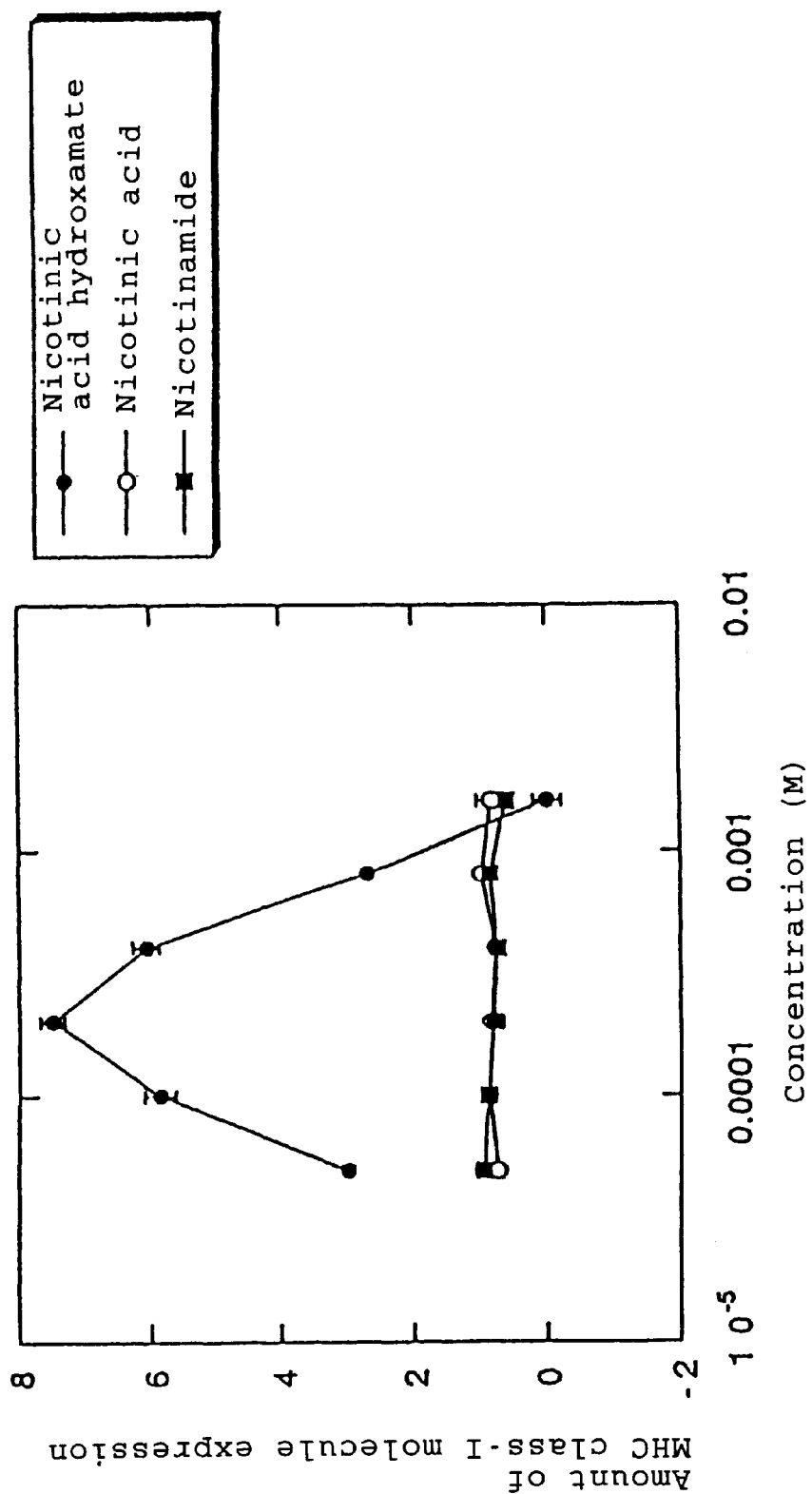
FIG. 5 shows the MHC class-I molecule expression promoting action of nicotinic acid and its derivatives, as well as their dependence on the concentration of addition.

Exemplary test results for cyclic tetrapeptide derivatives of the present invention and the positive control trichostatin A are shown FIGS. 3 and 4. In FIG. 3, the result of evaluation on the compound of the aforementioned Reference Example 1 is also shown. In addition, three compounds: nicotinic acid, nicotinamide and nicotinic acid hydroxamate as reference compounds were similarly evaluated and the results are shown in FIG. 5.

As shown in FIGS. 3 and 4, it was confirmed that all of the compound of Example 1 (HDA-5); cyclo(-Asu(NHOH)-Phe-Phe-D-Pro-), the compound of Example 2 (HDA-17); cyclo(-Aaz(NHOH)-Phe-Phe-D-Pro-), the compound of Example 3 (HDA-18); cyclo(-Api(NHOH)-Phe-Phe-D-Pro-), the compound of Example 4 (HDA-12); cyclo(-Asu (NHOH)-D-Phe-Leu-Pip-), and the compound of Example 5 (HDA-15); cyclo(-Asu(NHOH)-Aib-Phe-D-Pro-) exhibited MHC class-I molecule expression promoting action. Also, for the positive control trichostatin A, the MHC class-I molecule expression promoting action was confirmed as shown in FIG. 4. In particular, it was confirmed that the compound of Example 4 exhibited MHC class-I molecule expression promoting action even at a concentration of addition as low as trichostatin A. On the other hand, low MHC class-I molecule expression promoting action was observed only at a high concentration of addition of the compound of Reference Example 1; cyclo(-Asu(NHOH)-Phe-Phe-D-Pro)$_2$. Thus, the compound of Reference Example 1, which is a cyclic octapeptide derivative having the same structural units as the compound of Example 1, has an incomparably lower MHC class-I molecule expression promoting action than the compound of Example 1 which is a cyclic tetrapeptide derivative. In other words, it is concluded that although a side chain having a hydroxamic acid structure (hydroxyaminocarbonyl structure) at the end is of course important, the cyclic tetrapeptide structural portion makes an important contribution to the MHC class-I molecule expression promoting action. Based on results of these evaluation of the dependence of the aforementioned MHC class-I molecule expression promoting action on the concentration of addition, the concentration addition $C_{x2}$ at which the expression of MHC class-I molecule is twice that achieved without addition was determined. Part of the results is shown in Table 1.

TABLE 1

| Compound Tested | Twice Promoting Concentration $C_{x2}$ |
| --- | --- |
| Compound of Example 1 (HDA-5) | 135 nM |
| Compound of Example 2 (HDA-17) | 1120 nM |
| Compound of Example 3 (HDA-18) | 11600 nM |
| Compound of Example 4 (HDA-12) | 3.86 nM |
| Compound of Example 5 (HDA-15) | 36.2 nM |
| Compound of Reference Example 1 (HDA-19) | >40000 nM |
| Trichostatin A | 3.35 nM |

A review of the results with nicotinic acid and its derivatives that are given in FIG. 5 shows that MHC class-I molecule expression promoting action is found in the compound having a hydroxamic acid structure (hydroxyaminocarbonyl structure) and this provides a very strong corroboration for the fact that the side chain having a hydroxamic acid structure (hydroxyaminocarbonyl structure) at the end is a key to the MHC class-I molecule expression promoting action of the cyclic tetrapeptide derivatives according to the present invention.

From the comparison between the compounds of Examples 1 to 3, an optimum length of the methylene chain in said side chain having a hydroxamic acid structure (hydroxyaminocarbonyl structure) at the end was judged to be 5, which corresponded to the results with trapoxin derivatives. Probably, this difference in MHC class-I molecule expression promoting action due to the difference in the length of methylene chain may be presumed to be attributable to the presence of an optimum methylene chain length which depends on the distance between the site on histone deacetylase to be bound by the cyclic tetrapeptide portion of the cyclic tetrapeptide derivative of the present invention and the enzyme active site when said derivative acts on said enzyme. In addition, from the comparison with the side chain on N-acetylated lysine of the substrate, it may be assumed that another contributing factor is that the orientation of the oxygen atom in the carbonyl group at the enzyme active site is reversed depending upon the difference of the methylene chain length, more particularly depending upon whether it is odd- or even-numbered. Therefore, in an unsaturated hydrocarbon chain like trichostatins, the carbonyl group oxygen atom is retained in a more preferable orientation than in relatively flexible, saturated hydrocarbon chains, probably supplementing the difference of contribution of the cyclic tetrapeptide portion. Further, even if the contribution of the cyclic tetrapeptide portion is somewhat poor, those compounds which have an unsaturated hydrocarbon chain similar to the one in trichostatins may well be judged to exhibit an excellent overall MHC class-I molecule expression promoting action.

Further, similar to the dependence of nicotinic acid hydroxamate upon the concentration of its addition as shown in FIG. 5, the concentration-dependent increase of the MHC class-I molecule expression promoting activity of the cyclic tetrapeptide derivative according to the present invention has an apparent tendency to decrease in a range of higher concentrations. This phenomenon is interpreted as a result of the onset of inhibition of cell growth due to the inhibitory activity on histone deacetylase and the consequent inhibition of increase of the total amount of MHC class-I molecule expression. Thus, the inhibitory action on cell growth due to inhibitory activity on histone deacetylase is notably found in the higher concentration region.

Additionally, cyclic tetrapeptide compounds according to the present invention which were prepared in other Examples were also evaluated for MHC class-I molecule expression promoting activity. A plurality of assays were performed and the results on twice expression promoting concentrations are summarized in Table 2. In Table 2, the values for HDA-5, 17, 18, 12, 15 and 19 as well as trichostatin A shown in Table 1 are also shown.

is described as LLLD, the first L designating the base Asu(NHOH), isomers HDA-27, 38 and 39 in which the constituting amino acids are of the same types as in HDA-5 but the combination of their configuration differs are described as LDLD, LDLL and LLDL, respectively. These four stereoisomers HDA-5, 27, 38 and 39 have twice promoting concentrations of 98.2, 3.01, 558 and 65800 nM, respectively, and the order of the strength of their MHC class-I molecule expression promoting activities is LDLD>LLLD>LDLL>LLDL. Thus, in a case where Asu (NHOH) among the amino acid residues constituting the cyclic tetrapeptide takes the L-configuration, the cyclic amino acid residue adjoining to Asu(NHOH) preferably takes the D-configuration and, in addition, it is more preferable that the other amino acid residue adjoining to Asu

TABLE 2

| compounds | conc. for 2-fold expression (nM) | | |
|---|---|---|---|
| | mean | SD | N |
| trichostatin A | 2.81 | 1.95 | 14 |
| trichostatin C | 6.88 | 0.00 | 1 |
| trapoxin A | 3.59 | 0.00 | 1 |
| cyclo(-Aaz(NHOH)-Phe-Phe-D-Pro-) (CHAP17) | 990 | 168 | 3 |
| cyclo(-Api(NHOH)-Phe-Phe-D-Pro-) (CHAP18) | 10900 | 890 | 3 |
| cyclo(-Asu(NHOH)-Phe-Phe-D-Pro-) (CHAP5) | 98.2 | 23.3 | 11 |
| cyclo(-Asu(NHOH)-D-Phe-Phe-D-Pro-) (CHAP27) | 3.01 | 1.26 | 7 |
| cyclo(-Asu(NHOH)-D-Phe-Phe-Pro-) (CHAP38) | 558 | 97 | 4 |
| cyclo(-Asu(NHOH)-Phe-D-Phe-Pro-) (CHAP39) | 65800 | 6050 | 3 |
| cyclo(-Asu(NHOH)-Phe-Phe-Sar-) (CHAP40) | 748 | 337 | 7 |
| cyclo(-Asu(NHOH)-D-Phe-Phe-Sar-) (CHAP41) | 24.5 | 15.6 | 3 |
| cyclo(-Asu(NHOH)-D-Phe-Ala-D-Pro-) (CHAP45) | 23.1 | 3.5 | 3 |
| cyclo(-Asu(NHOH)-D-Pro-Phe-D-Phe-) (CHAP37) | 320 | 52 | 4 |
| cyclo(-Asu(NHOH)-Phe-Phe-D-Pro-)2 (CHAP19) | weak | | 3 |
| cyclo(-Asu(NHOH)-D-Phe-Ile-D-Pro-) (CHAP46) | 1.96 | 0.53 | 3 |
| cyclo(-Asu(NHOH)-D-Naf-Ile-D-Pro-) (CHAP47) | 9.59 | 12.17 | 9 |
| cyclo(-Asu(NHOH)-D-Pya-Ile-D-Pro-) (CHAP48) | 0.846 | 0.956 | 4 |
| cyclo(-Lys(Ac)-Phe-Phe-D-Pro-) (CHAP5-Ac) | 240000 | 0 | 1 |
| cyclo(-Lys(Ac)-Phe-Phe-D-Pro-)2 (CHAP5-Ac)2 | 75000 | 0 | 1 |
| cyclo(-Lys(BrAc)-Phe-Phe-D-Pro-) (CHAP5-BrAc) | 5660 | 0 | 1 |
| cyclo(-Asu(NHOH)-D-Tyr(Me)-Ile-Pro-) (CHAP30) | 16.9 | 8.2 | 4 |
| cyclo(-Asu(NHOH)-D-Tyr(Me)-Ile-D-Pro-) (CHAP31) | 1.41 | 0.51 | 6 |
| cyclo(-Api(NHOH)-D-Tyr(Me)-Ile-D-Pro-) (CHAP42) | 512 | 247 | 5 |
| cyclo(-Aaz(NHOH)-D-Tyr(Me)-Ile-D-Pro-) (CHAP43) | 155 | 66 | 5 |
| cyclo(-Asu(NHOH)-D-Tyr(Me)-Ile-Pip-) (CHAP49) | 5.30 | 2.16 | 9 |
| cyclo(-Asu(NHOH)-D-Tyr(Me)-Ile-D-Pip-) (CHAP50) | 0.203 | 0.099 | 7 |
| cyclo(-Asu(NHOH)-D-Tyr(Me)-Ile-Tic-) (CHAP51) | 10.97 | 3.05 | 6 |
| cyclo(-Asu(NHOH)-D-Tyr(Me)-Ile-D-Tic-) (CHAP52) | 0.191 | 0.103 | 4 |
| cyclo(-Asu(NHOH)-D-Tyr(Me)-Ala-D-Pro-) (CHAP44) | 35.00 | 4.80 | 3 |
| cyclo(-Asu(NHOH)-D-Tyr(Me)-Ile-Pro-)2 (CHAP14) | >10000 | | 1 |
| cyclo(-Asu(NHOH)-D-Phe-Leu-Pro-) (CHAP28) | 80.2 | 19.6 | 4 |
| cyclo(-Asu(NHOH)-D-Phe-Leu-D-Pro-) (CHAP29) | 5.41 | 1.72 | 4 |
| cyclo(-Asu(NHOH)-D-Phe-Leu-D-Pip-) (CHAP12) | 2.75 | 1.44 | 5 |
| cyclo(-Asu(NHOH)-D-Phe-Leu-Pip-) (CHAP53) | 19.8 | 4.1 | 3 |
| cyclo(-Asu(NHOH)-Lys(Boc)-Phe-D-Pro-) (CHAP32) | 773 | 244 | 2 |
| cyclo(-Asu(NHOH)-Trp-Leu-D-Pip-) (CHAP33) | weak | | 2 |
| cyclo(-Asu(NHOH)-D-Pro-Ala-D-Ala-) (CHAP13) | 406 | 86 | 3 |
| cyclo(-Asu(NHOH)-Aib-Phe-D-Pro-) (CHAP15) | 33.2 | 8.7 | 3 |
| cyclo(-Asu(NHOH)-Trp(CHO)-Leu-D-Pip-) (CHAP16) | toxic | | 2 |
| Ac-Asu(NHOH)-NH-Bzl | 2410 | 771 | 3 |
| Ph-(CH2)5-CONHOH | 11400 | 0 | 1 |
| nicotinic acid hydroxamate | 28000 | 0 | 2 |
| benzohydroxamic acid | 35800 | 2480 | 2 |
| benzoic acid | >200000 | | 1 |
| nicotinamide | >1000000 | | 1 |
| nicotinic acid | >1000000 | | 1 |

Referring to the results of Table 2, the aforementioned suitable selections of configuration of the four amino acid residues constituting the cyclic tetrapeptide of the present invention can be verified by comparison between stereoisomers which differ only in their configuration. As an example, if the configuration of HDA-5, where Asu(NHOH) having a hydroxamic acid structure on the side chain which is characteristic of the cyclic tetrapeptide takes the L-configuration, (NHOH) also takes the D-configuration. Similarly, in the comparisons between HDA-30 (LDLL) and HDA-31 (LDLD), between HDA-28 (LDLL) and HDA-29 (LDLD), between HDA-53 (LDLL) and HDA-12 (LDLD), between HDA-40 (LDLL) and HDA-50 (LDLD), and between HDA-51 (LDLL) and HDA-52 (LDLD), the cyclic amino acid residue adjoining to the amino acid residue having a hydroxamic acid structure on the side chain preferably takes the D-configuration and, in addition, it is more preferable that the other adjoining amino acid residue thereto also takes the D-configuration.

In the results of evaluation of histone deacetylase inhibitory activity that are shown in Test Example 4, a similar order of inhibitory activities was verified: HDA-27 (LDLD) >HDA-5 (LLLD), HDA-31 (LDLD)>HDA-30 (LLLD), and HDA-29 (LDLD)>HDA-28 (LLLD). However, the difference in the histone deacetylase inhibitory activity is not as notable as the difference in the MHC class-I molecule expression promoting activity.

To exhibit the MHC class-I molecule expression promoting action, the cyclic tetrapeptide should be transported from the outside of a cell into the inside of the cell. Or, it may also be supposed that the maintenance of acetylation in the specific lysine contained the acetylated histone is more important. Thus, it may be assumed that factors other than the histone deacetylase inhibitory activity, such as the process of transport into a cell, causes the aforementioned difference.

However, from these comparisons, it is judged that when the action of interest is particularly on a cell per se, the LDLD-type is more satisfactory than LLLD and LDLL which are combinations of configurations found in naturally occurring cyclic tetrapeptides that show histone deacetylase inhibitory activity.

Test Example 2
Inhibitory effect on histone deacetylation

In order to prove that the MHC class-I molecule promoting action of the cyclic tetrapeptide derivative according to the present invention is associated with inhibitory effects on histone deacetylation, the effects of inhibiting the histone deacetylation in the aforementioned B16/BL6 cells were verified.

Test Method

In a culture flask of 75 ml in capacity, $1.5 \times 10^5$ B16/BL6 cells were inoculated and preliminarily cultured for 4 days. Then, a given amount of a compound to be tested was added and subsequently cultured for 6 hours. Thereafter, cells were striped using 0.25% trypsin enzyme solution, washed once with PBS and stored temporarily at $-80°$ C.

From this cell sample, histone was separated from chromatin and collected together with other proteins in a conventional manner. The resulting protein sample was subjected to AUTgel electrophoresis in an amount of 1 $\mu$g/lane. Said gel was stained with silver to detect bands separated by the migration.

Figure 6:
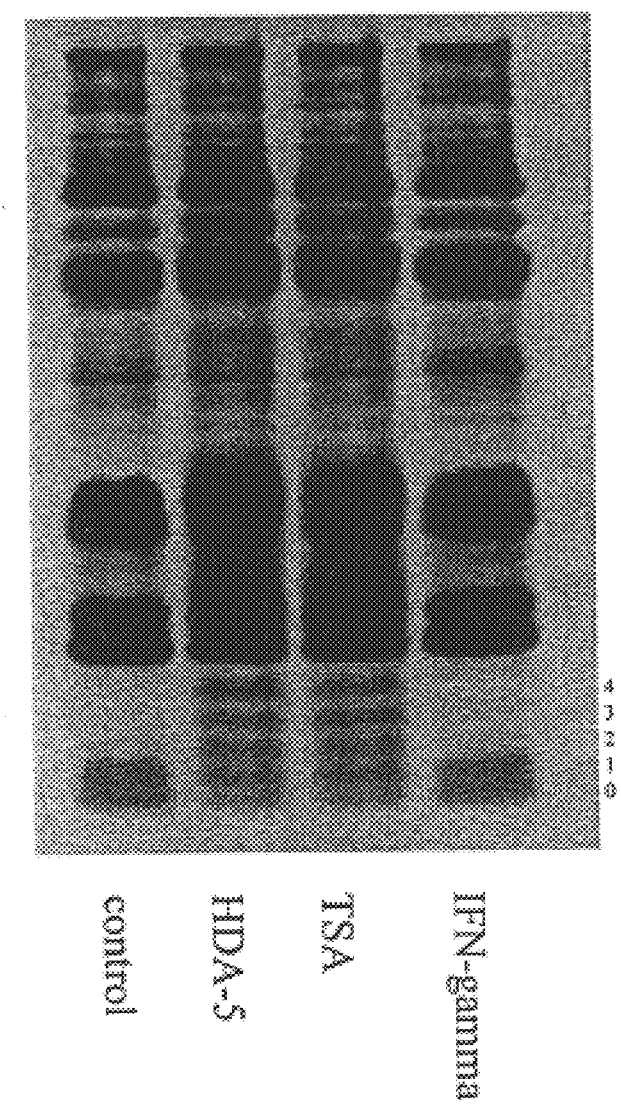
FIG. 6 shows the effect of inhibiting histone deacetylation in B16/BL6 cells by the addition of the compound of Example 1 and trichostatin A.

As an example, a comparison between the results on the compound of the aforementioned Example 1 which was added at 10 $\mu$M, trichostatin A added at 1 $\mu$M, and INF-$\gamma$ added at 100 U/ml is shown in FIG. 6. The result on a control group to which no compound to be tested was added is also shown. In FIG. 6, a band of histone H4 is seen in the lowermost region; however, a total of 5 discrete bands are clearly seen in this region according to the results of addition of trichostatin A and the compound of Example 1. Compared with the no-addition control, three of said 5 bands were not seen in the control, indicating that they were N-acetylated histones with different degrees of deacetylation.

Thus, it has been found that like trichostatin A having deacetylase enzyme inhibiting activity, the addition of the compound of Example 1 inhibits the deacetylation of histone, causing highly acetylated histones to remain. It has been verified that the addition of the cyclic tetrapeptide derivative according to the present invention has an inhibitory effect on histone deacetylation and that the MHC class-I molecule expression promoting action is ancillary to the effect.

Test Example 3
Inhibitory effect on cell proliferation

In order to verify the action of the cyclic tetrapeptide derivative according to the present invention in inhibiting cell proliferation in cancerized cells, the action on the proliferation of the aforementioned B16/BL6 cells was investigated. The evaluation of cell proliferation rates was done utilizing a commercially available measuring kit, specifically, from Promega under the trade name CellTiter 96 Aqueous Non-Radioactive Proliferation Assay Kit. In the measuring kit, the amount of products through reduction of a reagent tetrazolium compound (3-(4,5-dimethylthiazol-2-yl)-5-(3-carboxymethoxyphenyl)-2-(4-sulfophenyl)-2H-tetrazolium, inner salt; MTS) by viable animal cells is determined by detecting spectrophotometrically the color generated from the products. Since the amount of products is proportional to the amount of viable cells, this kit is utilized to evaluate the amount of viable cells.

Test Method

According to the procedure of Test Example 1, B16/BL6 cells are inoculated in a 96 well microplate and cultured for 24 hours. Then, 10 $\mu$l of a solution of the source solution of a compound to be tested which has been diluted to a predetermined amount per well is added. Thereafter, culture is continued for additional 48 hours and 20 $\mu$l of a reagent solution in the aforementioned CellTiter 96 Aqueous Non-Radioactive Proliferation Assay Kit is then added. After incubation is continued at $37°$ C. for 1 hour, the amount of color generation is measured as an absorbance at 490 n musing a microplate reader.

The amount of cell proliferation of a group to which a compound to be tested is added is expressed in a relative value as compared to the standard cell proliferation (100%) in a control group to which no compound to be tested is added. For each compound tested, the amounts of cell proliferation were measured at different concentrations of addition and the dependence of the quantitative cell proliferation on the concentration of addition was investigated. From the results, a concentration of addition at which the amount of cell proliferation was inhibited by 50% relative to the amount of cell proliferation in the control group without addition was determined.

Part of the results of evaluation for 50% inhibiting concentrations in the proliferation of the aforementioned B16/BL6 cells is shown in Table 3, which also shows the result of evaluation on trichostatin A as a positive control which has been reported to exhibit cell proliferation inhibiting action on cancer cells.

TABLE 3

| Compound tested | 50% inhibiting concentration |
| --- | --- |
| Compound of Example 1 (HDA-5) | 210 nM |
| Compound of Example 4 (HDA-12) | 12.3 nM |
| Compound of Example 5 (HDA-15) | 92.5 nM |
| Trichostatin A | 14.3 nM |

As seen from Table 3, the cyclic peptide derivatives of the present invention exhibit cell proliferation inhibiting action in a concentration region higher than the concentrations at which the promotion of MHC class-I molecule expression exemplified in Table 1 is achieved. The compound of Example 4 exhibits the cell proliferation inhibiting action at a lower concentration than trichostatin A; due to this effect, the apparent amount of promotion tends to saturate in the aforementioned results of evaluation of the MHC class-I molecule expression promoting action.

Further, it was verified that the cyclic peptide derivatives of the present invention inhibited the proliferation of not only B16/BL6 cell line used in the above test example but also other cancerized cells. The test method was in accordance with the above-mentioned procedure, except that the period of incubation after the addition of a compound was 72 hours.

As illustrative examples, results are shown for an evaluation using mouse malignant melanoma B16/BL6 and B16 cell lines; leukemia L1210 cell line, colon cancer Colon26 cell line, and liver cancer MH134 cell line as cancer cells. For the cell proliferation inhibiting action of each compound tested for these cancer cells, 50% proliferation inhibiting concentrations are shown in Table 4. Also, the results on trichostatin A are shown in Table 4.

As a substrate, [$^3$H]acetyl histone was used. In a culture solution of FM3A cells in the presence of 5 mM sodium n-butyrate, [$^3$H]acetate was added, followed by incubation for 30 minutes to radio-label the histone. The histone was prepared in a conventional manner and used as a substrate solution.

An assay was performed by adding a compound to be tested at a given concentration while using a no-addition

TABLE 4

| compounds | L1210 (nM) | | B16/BL6 (nM) | | B16 (nM) | | Colon 26 (nM) | | MH134 (nM) | |
|---|---|---|---|---|---|---|---|---|---|---|
| | mean | SD | mean | SD | mean | SD | mean | SD | mean | SD |
| HDA-17 | 7380 | 1160 | 1260 | 210 | 23500 | 5000 | 29300 | 23900 | 19900 | 8410 |
| HDA-18 | >100000 | | 59300 | 17300 | >100000 | | >100000 | | >100000 | |
| HDA-13 | 2770 | 950 | 866 | 203 | 15400 | 4700 | 11000 | 1600 | 7920 | 2300 |
| HDA-5 | 500 | 96 | 257 | 35 | 3370 | 1030 | 2160 | 280 | 1660 | 763 |
| HDA-28 | 1330 | 1371 | 470 | 54 | 3820 | 1660 | 7370 | 1090 | 4830 | 2050 |
| HDA-30 | 480 | 255 | 112 | 3 | 861 | 282 | 1570 | 270 | 1510 | 106 |
| HDA-15 | 193 | 122 | 110 | 1 | 1230 | 630 | 908 | 144 | 946 | 262 |
| HDA-27 | 53.0 | 21.7 | 18.0 | 2.5 | 309 | 95 | 277 | 62 | 236 | 59 |
| HAD-31 | 18.8 | 5.4 | 5.43 | 0.39 | 44.2 | 22.3 | 33.0 | 12.0 | 50.7 | 8.9 |
| HDA-29 | 43.8 | 19.9 | 15.8 | 5.6 | 293 | 109 | 198 | 51 | 176 | 87 |
| HDA-12 | 28.3 | 13.6 | 9.44 | 3.11 | 262 | 174 | 149 | 39 | 112 | 48 |
| TSA | 12.4 | 2.4 | 19.1 | 10.5 | 621 | 50 | 139 | 42 | 41.7 | 23.6 |

In the range of comparisons shown here, there is also found a coincidence in the order of activities of the compounds between the inhibitory effect on cell proliferation and the MHC class-I molecule expression promoting action. It has been found that in the inhibitory effect on cell proliferation, the sensitivity of some compounds significantly differs with cancer cells species, indicating that the effect does not always coincide quantitatively with the MHC class-I molecule expression promoting action. Among the cyclic tetrapeptides of the present invention compared in this example, HDA-31 exhibits significantly higher proliferation inhibiting action than the others, with its $IC_{50}$ values against all cancer cells tested ranging from several nM to several tens of nM.

Test Example 4
Histone Deacetylase Enzyme Inhibiting Activity

For the purpose of obtaining a proof that the inhibitory effect on histone deacetylation in the cell lines in the aforementioned Test Example 2 was indeed derived from the inhibition of the enzyme activity of histone deacetylase by the cyclic tetrapeptide compounds of the present invention, it was verified in the following evaluation that the cyclic tetrapeptide compounds of the present invention inhibited the enzyme activity of histone deacetylase in an in vitro system.

Evaluation Method

In an enzyme system using a radio-labelled acetylated histone as a substrate, histone deacetylase enzyme inhibiting activity was evaluated. The basic conditions were in accordance with the method of Yoshida et al. (J. Biol. Chem., 265, 17174–17179, 1990).

Mouse histone deacetylase to be used was partially purified from FM3A cells. Cells were suspended in HDA buffer (15 mM potassium phosphate, 5% glycerol, 0.2 mM EDTA, pH 7.5), homogenized and centrifuged (35000×g, 10 min) to collect the nuclei which in turn were homogenized in the same buffer containing 1 M $(NH_4)_2SO_4$. After ultrasonic disruption and centrifugation, the concentration of $(NH_4)_2SO_4$ in the supernatant was increased to 3.5 M to precipitate deacetylase enzyme proteins. This precipitate was redissolved in HDA buffer, dialyzed against HDA buffer, applied to DEAE-cellulose column and eluted in NaCl gradient. Active fractions were used as a histone deacetylase enzyme solution.

control group, and by incubating the substrate solution and the enzyme solution at 37° C. for 10 minutes (reaction volume, 100 µl). The enzyme reaction was stopped by adding 10 µl of concentrated hydrochloric acid and the excised [$^3$H]acetate was extracted with ethyl acetate for radioactivity measurement. The inhibiting activity was expressed by a concentration at which the enzyme activity in the control group was inhibited by 50% (50% inhibiting concentration).

As seen from Table 5 which shows part of the evaluation results, all cyclic tetrapeptide compounds tested of the present invention exhibited histone deacetylase inhibiting activity. Further, the compounds have a side chain hydroxamic acid structure, and it was also confirmed that the inhibition on the enzyme histone deacetylase was reversible.

TABLE 5

Effect of histone deacetylase inhibiting substances

| | Compound tested | $IC_{50}$ (nM) |
|---|---|---|
| | Sodium n-butyrate | 119,000 |
| | Trapoxin A | 0.47 |
| | Trichostatin A | 1.44 |
| Example 10 | HDA-6 | 27,800 |
| Example 1 | HDA-5 | 2.18 |
| Example 2 | HDA-17 | 19.8 |
| Example 3 | HDA-18 | 390 |
| Example 20 | HDA-27 | 1.45 |
| Example 19 | HDA-28 | 6.04 |
| Example 22 | HDA-29 | 1.59 |
| Example 23 | HDA-30 | 4.90 |
| Example 21 | HDA-31 | 2.08 |
| Example 9 | HDA-32 | 4.95 |

As in the results of evaluation of MHC class-I molecule expression promoting action in the cell line of Test Example 1, if, with in the side chain hydroxamic acid structure characteristic of the cyclic tetrapeptides according to the present invention, the ring structure is same, optimal inhibiting activity is obtained with the methylene chain length of the side chain being 5, as in HDA-5, while both HDA-17 having 6 carbon atoms in the chain and HDA-18 having 4 carbon atoms in the chain exhibit less inhibiting activity than the compound having 5 carbon atoms in the chain although their activity is considerably high. This coincidence also leads to a conclusion that the MHC class-I molecule expression promoting action of the cyclic tetrapeptides according to the present invention is derived from the histone deacetylase inhibiting activity.

Test Example 5
Histone Deacetylase Enzyme Inhibiting Activity (Evaluation Using Synthetic Peptide Substrate)

In the aforementioned Test Example 4, the histone deacetylase enzyme inhibiting activity of the cyclic tetrapeptide compounds according to the present invention was evaluated using histone harvested from cells. In order to complement the results, the histone deacetylase enzyme inhibiting activity was evaluated again using a synthetic peptide substrate.

Test Method

The preparation of histone deacetylase was performed essentially according to the method of Yoshida et al. (J. Biol. Chem., 265,17174–17179, 1990). The enzyme to be used was partially purified from B16/BL6 cells. The cells were suspended in HDA buffer (15 mM potassium phosphate, 5% glycerol, 0.2 mM EDTA, 10% 2-mercaptoethanol, pH 7.5), homogenized and centrifuged (2500×g, 10 min) to collect the nuclei, which in turn were homogenized in the same buffer containing 1 M $(NH_4)_2SO_4$. After ultrasonic disruption and centrifugation, the concentration of $(NH_4)_2SO_4$ in the collected supernatant was increased to 3.5 M to precipitate histone deacetylase. This precipitate was redissolved in HDA buffer, subjected to gel filtration to replace the solvent with HDA buffer, and used as a crude histone deacetylase enzyme solution.

As a substrate, a synthetic substrate peptide, $[^3H]$ acetylated histone H4 peptide was used. This $[^3H]$acetylated histone H4 peptide was obtained by synthesizing the N-terminal peptide of histone H4; SGRGKGGKGLGKG-GAKRHRKVC (the C-terminal being cysteine) and radio-acetylating with $^3H$ -acetic anhydride.

An assay was performed by incubating the synthetic substrate solution and the enzyme solution at 37° C. for 3 hours in the presence of a compound to be tested (reaction volume, 100 μl). The reaction was stopped by adding 25 μl of 1 M HCl and 0.2 M acetic acid and $[^3H]$acetate excised by the enzyme reaction was extracted with ethyl acetate for radioactivity measurement. As a control group, the same procedure was repeated without addition of any test compound to the reaction system. The inhibiting activity was expressed by a concentration at which the histone deacetylase enzyme activity in the control group was inhibited by 50% (50% inhibiting concentration).

Part of the evaluation results is shown in Table 6. There is found some inconsistency between the results using the natural acetylated histone as a substrate and the synthetic substrate. However, it is verified from all results that the cyclic tetrapeptides shown in Table 6 are all excellent in histone deacetylase enzyme inhibiting activity.

Comparing these results with the MHC class-I molecule expression promoting activity and cell proliferation inhibiting action found in the cell level, it has been found that although the cyclic tetrapeptides having higher enzyme inhibiting activity show high levels of MHC class-I molecule expression promoting activity and cell proliferation inhibiting action, the order in the strength of their activities is not always consistent with the order in the strength of enzyme inhibiting activities.

It may be judged that the MHC class-I molecule expression promoting activity and cell proliferation inhibiting action associated with the histone deacetylase enzyme inhibiting activity in cells may substantially be affected by any difference in the cell membrane permeability of the compound concerned in addition to the enzyme inhibiting activity, and accordingly, some compounds may not have very high levels of MHC class-I molecule expression promoting activity and cell proliferation inhibiting action.

TABLE 6

| Compound | $IC_{50}$ (nM) |
| --- | --- |
| Trichostatin A | 2.55 |
| HDA-5 | 6.03 |
| HDA-30 | 3.31 |
| HDA-31 | 3.32 |
| HDA-49 | 4.81 |
| HDA-50 | 3.96 |
| HDA-51 | 49.8 |
| HDA-52 | 4.35 |
| HDA-17 | 24.7 |
| HDA-18 | 150 |
| HDA-27 | 3.44 |
| HDA-38 | 5.32 |
| HDA-39 | 226 |
| HDA-37 | 9.16 |
| HDA-42 | 53.8 |
| HDA-43 | 33.9 |

Test Example 6
Evaluation of Anti-cancer Activity

Since the cyclic tetrapeptide compounds of the present invention exhibited cell proliferation inhibiting effect on cancerized cells in vitro as shown in the results of the aforementioned Test Example 3, it may be concluded that they will also have anti-cancer activity in vivo. On the other hand, the cell proliferation inhibiting effect on individual cancer cells was observed in different degrees and it is supposed that there may be a difference in the sensitivity to individual cancer cells. In order to prove that the cyclic tetrapeptide compounds of the present invention indeed exhibit anti-cancer activity in the actual living body and to verify the presence or absence of any difference in sensitivity to individual cancer cells, typical cancer cells were used in evaluating anti-cancer activity in both ascites and solid tumor systems.

(1) In Vivo Anti-cancer Activity in Mouse (Ascites Tumor System)

Test Method

With respect to an ascites tumor system, in vivo anti-cancer activity of the cyclic tetrapeptide compounds according to the present invention was evaluated using cancer-carrying mouse. The cancer cells used were L1210, B16, Colon26 and MH134. These cancer cells were cultured in a conventional manner and suspended in PBS, and $10^5$ cells of L1210, or $10^6$ cells of B16, Colon26 or MH134 were intraperitoneally transplanted into each mouse (100 μl/mouse). The mouse used was CDF1, BDF1, CDF1 or C3H/HeN (male, 7 weeks in age) for L1210, B16, Colon 26or MH134, respectively. Drug administration was started from the day next to the transplantation of cancer cells. For L1210, 0.5% carboxymethyl cellulose Na suspension and for other cancer cells, PBS solution (actually, as suspension neutralized with NaOH) were continuously administered everyday (100 μl/mouse). The period of administration was 4 days for L1210, 9 days for B16 and MH134, and 8 days for Colon26.

After the administration period passed, the mice administered were bred and median survival days were calculated on the basis of the number of days from the transplantation of cancer cells to death. The percent ratio (T/C%) between the median survival days (C) for a control group to which an equal amount of a drug-free solution was administered and the median survival days (T) of the treated group administered with the drug was determined. As an example, the results for HDA-31 are shown in Table 7.

TABLE 7

| cell lines | Median Survival days (T/C %) | | | |
|---|---|---|---|---|
| | 0.015 mg/mouse | 0.05 mg/mouse | 0.15 mg/mouse | 1.5 mg/mouse |
| L1210 | 113 | | <u>125</u> | 37.5 |
| B16 | 117 | 119 | <u>139</u> | |
| Colon26 | 90.9 | 86.4 | 63.6 | |
| MH134 | 95.8 | 85.4 | 91.7 | |

From the results shown in Table 7, HDA-31 obviously exhibited a life-saving effect for the cancer cells L1210 and B16. On the other hand, no life-saving effect was observed for Colon26 and MH134. It has thus been suggested that the cyclic tetrapeptide compounds of the present invention may possibly be anti-cancer agents for ascites tumor systems although the effectiveness is variable with the kind of cancer.

(2) In Vivo Anti-cancer Activity in Mouse (Solid Tumor System)

Test Method

Three mouse cancers Colon26, Meth A and B16 were used to evaluate in vivo anti-cancer activity of the cyclic tetrapeptide compounds according to the present invention in a solid tumor system. The cancer cells were cultured in a conventional manner, suspended in PBS and intradermally transplanted into a mouse ventral portion ($10^5$). The mouse used was CDF1, Balb/c or BDF1 (male, 7 weeks in age) for Colon 26, Meth A or B16, respectively. On day-4, 7 and 10 for Colon 26, or on day-7, 10, 13 and 16 for Meth A and B16 (day-0 being the day of cancer transplantation), a given amount of solution containing a predetermined amount of a compound to be tested was administered into the tail vein (10, 3 and 1 mg/kg; 2 ml/kg). In this example, the solution for administration used was PBS suspension (as neutralized with NaOH). On day-14 for Colon26 and on day-21 for Meth A and B16, the size of tumor (shorter and longer diameters) was measured. The tumor weight was estimated from the value obtained by calculation from the equation: ½×longer diameter×shorter diameter$^2$. Anti-tumor effects were based on the estimated tumor weight used as a measure and a tumor weight was estimated for a control group to which an equal amount of a drug-free solution was added; % inhibition was determined on the basis of the difference between the estimated tumor weights for the treated and control groups.

As an example, the evaluation results for HDA-31 are shown in Table 8.

TABLE 8

| cell lines | condition | tumor weight (mg) | % inhibition |
|---|---|---|---|
| Colon 26 | control | 980 ± 77 | |
| | 1 mg/kg | 756 ± 25 | 22.9 |
| | 3 mg/kg | 677 ± 155 | 31.0 |
| | 10 mg/kg | 726 ± 123 | 25.9 |
| Meth A | control | 3120 ± 480 | |
| | 1 mg/kg | 2100 ± 570 | 32.5 |
| | 3 mg/kg | 1230 ± 500 | 60.7 |
| | 10 mg/kg | 1470 ± 500 | 52.8 |
| B16 | control | 699 ± 229 | |
| | 1 mg/kg | 258 ± 184 | 63.1 |
| | 3 mg/kg | 280 ± 152 | 59.9 |
| | 10 mg/kg | 120 ± 112 | 82.9 |

From the results shown in FIG. 8, it has been confirmed that the cyclic tetrapeptide compounds of the present invention including HDA-31 exhibit effectiveness in the solid tumor cells tested. In particular, HDA-31 showed a very high inhibition rate of 80% against B16 melanoma.

It has been judged from the above results that the cyclic tetrapeptide compounds of the present invention show anti-cancer activity in both ascites and solid tumor systems by utilizing their action in inhibiting the proliferation of cancer cells. Further, anti-cancer activity was observed when the drug was administered to the tail vein in the above example, and it may be judged that after the administration of the drug, its concentration in the blood was maintained within an effective range over a considerable period of time to exhibit the anti-cancer effect.

Test Example 7

It may be judged that the concentration of the cyclic tetrapeptides of the present invention in the blood is maintained within an effective range over a considerable period of time after their administration; in addition, it has been verified that such change of concentration in blood which is suitable for actual application as an anti-cancer agent is achieved. As an example, the results of evaluation of the drug HDA-31 used in the above Test Examples are shown.

Change of Concentration of HDA-31 in Rat Blood

Test Method

Under anesthesia with Ketamine/Kylazine mixture, SD rats were administered with HDA-31 into the tail vein (10 mg/kg; 2 ml/kg). The drug was dispersed in PBS and neutralized with NaOH and the resulting suspension was used. After administration, blood was taken from the carotid artery at a given interval of time (using heparin as an anti-coagulant) and centrifuged to prepare plasma. HDA-31 in the plasma was extracted with MTBE (methyl-t-butyl-ether) and separated by reverse-phase HPLC and a peak area corresponding to HDA-31 was quantitatively determined with a mass spectrometer.

Figure 7:
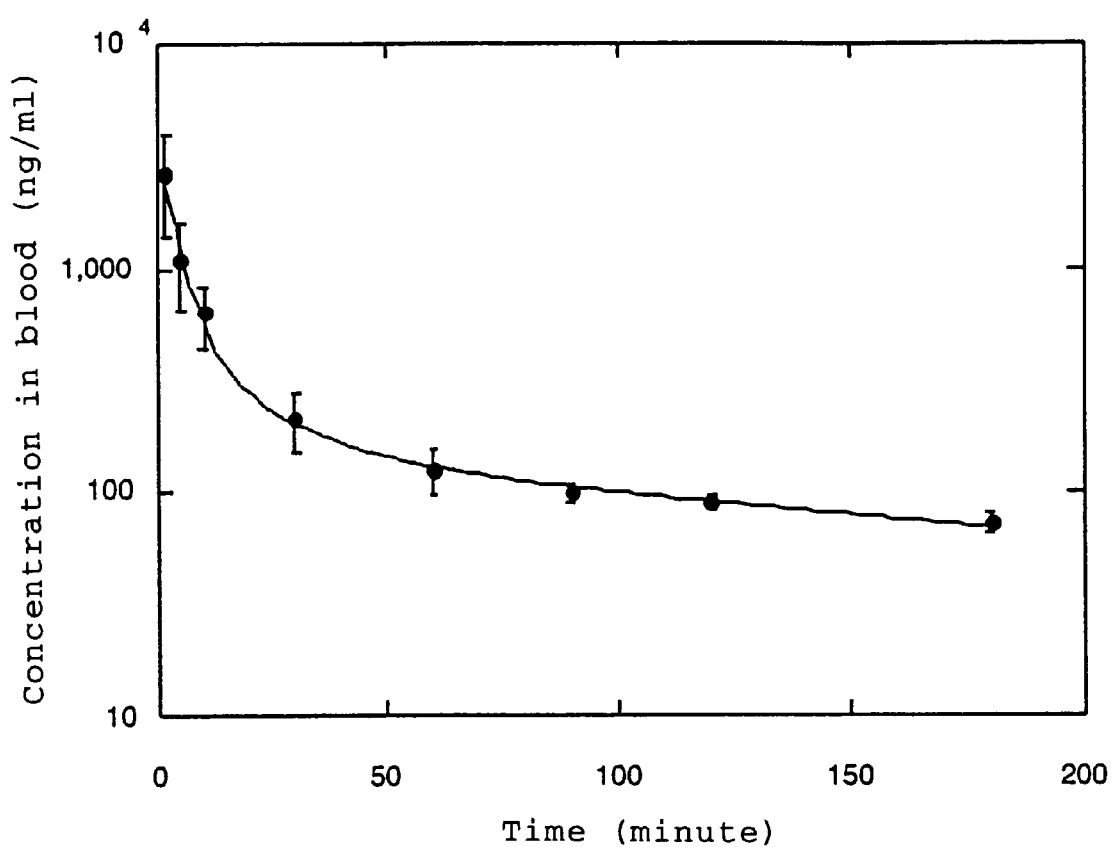
FIG. 7 shows the change of concentration of the compound of Example 21: HDA-31 in blood after administration thereof into mouse tail vein.

The results are shown in FIG. 7. The results shown are mean values for 3 animals. $IC_{50}$ value of HDA-31 for cancer cell proliferation inhibition range from several nM to several tens of nM. Since 100 ng/ml corresponds to 174 nM in molar concentration, it can be seen that concentrations in blood exceeding the stated effective concentrations were maintained over a few hours after the intravenous administration.

Since the drug was administered as a suspension of fine particles, the fine particulate drug may possibly be rapidly metabolized without being fully circulated in the blood. Taking this possibility into consideration, it can be expected that if a medium capable of completely dissolving the drug is used, higher concentrations in the blood may be achieved at the same dose. With respect to the inhibition of cancer cell proliferation or promotion of MHC class-I molecule expression, HDA-50 and HDA-52, for example, exhibit higher activities than HDA-31 as shown in the aforementioned results of the tests at the cell level. Assuming that the cyclic tetrapeptide compounds of the present invention that exhibit higher activities than HDA-31, such as HDA-50 and HDA-52, show similar kinetics to HDA-31 shown here, these compounds could achieve an effective concentration in blood at lower doses.

Industrial Applicability

The cyclic tetrapeptide derivatives or pharmaceutically acceptable salts thereof according to the present invention have an excellent activity in promoting the MHC class-I molecule expression as an ancillary effect of their excellent histone deacetylase enzyme inhibiting activity. Further, they also have a cell proliferation inhibiting and cell cycle inhibiting action derived from the enzyme histone deacety lase inhibition, so that enlargement of cancer tissues is inhibited. Hence, by utilizing the MHC class-I molecule expression promoting action, they can remarkably promote the elimination of cancer cells by the immune system and are very useful as anti-cancer agents. Since the enzyme histone deacetylase inhibition of the cyclic tetrapeptide derivatives according to the present invention is reversible, they have the advantage of causing very little unfavorable side effects, such as cell proliferation inhibition and cell cycle inhibiting action, on normal tissues as compared with irreversible inhibitors.

What is claimed is:

1. A cyclic tetrapeptide derivative represented by any of the following general formulae (I), (I'), (I''), and (I'''):

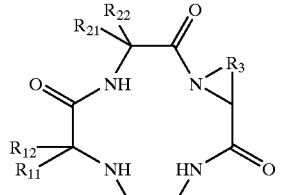
(I)

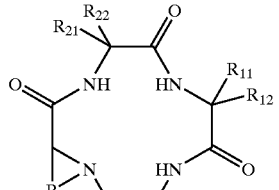
(I')

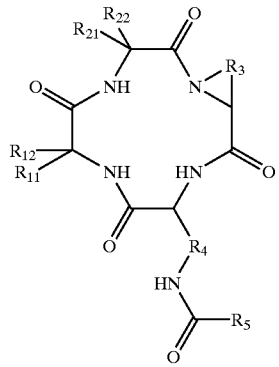
(I'')

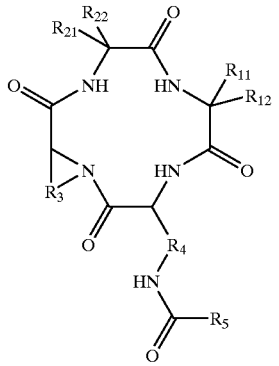
(I''')

wherein:

$R_{11}$, $R_{12}$, $R_{21}$ and $R_{22}$ independently denote a monovalent group selected from hydrogen, a linear alkyl group with 1 to 6 carbon atoms, a branched alkyl group with 3 to 6 carbon atoms, a linear ω-aminoalkyl group with 1 to 5 carbon atoms, a branched aminoalkyl group with 3 to 5 carbon atoms, an N-acyl-aminoalkyl group which is formed by substituting the amino group on said linear ω-aminoalkyl or branched aminoalkyl groups with an acyl group or a halogeno-substituted acyl group that has 3 or less carbon atoms, a benzyl group, a 4-methoxybenzyl group, a 3-indolylmethyl group, an (N-methoxy-3-indolyl)methyl group, an (N-acyl-3-indolyl)methyl group having an acyl group with 3 or less carbon atoms as a substituent on the ring-forming nitrogen atom, and a methyl group substituted with an aryl group comprising 4 or less rings;

$R_3$ denotes a divalent group selected from a linear alkylene group with 3 or 4 carbon atoms in the chain which may have a branched chain on the chain; a linear alkenylene group with 3 or 4 carbon atoms in the chain which may have a branched chain on the chain; a linear alkadienylene group with 4 carbon atoms in the chain which may have a branched chain on the chain; a divalent group in which the branched chain added onto said linear alkylene, linear alkenylene or alkadienylene group forms a fused ring structure; and a divalent group in which among the carbon atoms constituting the linear alkylene, linear alkenylene or alkadienylene group, one of the carbon atoms other than that having a free valence has been replaced with a heteroatom oxygen, sulfur or nitrogen;

$R_4$ denotes a divalent group having a chained hydrocarbon group with 4 to 6 carbon atoms in the chain which may have a branched chain on said chain, or a divalent group in which among the carbon atoms constituting the chained hydrocarbon group, at least one of the carbon atoms other than that having a free valence has been replaced with a heteroatom oxygen, sulfur or nitrogen; and $R_5$ in the general formulae (I") or (I'") denotes a methyl group or halogeno-substituted methyl group, or a pharmaceutically acceptable salt thereof.

2. The cyclic tetrapeptide derivative according to claim 1, which is represented by said general formula (I), or a pharmaceutically acceptable salt thereof.

3. The cyclic tetrapeptide derivative according to claim 1, which is represented by said general formula (I'), or a pharmaceutically acceptable salt thereof.

4. The cyclic tetrapeptide derivative according to claim 1, which is represented by said general formula (I"), or a pharmaceutically acceptable salt thereof.

5. The cyclic tetrapeptide derivative according to claim 1, which is represented by said general formula (I'"), or a pharmaceutically acceptable salt thereof.

6. A histone deacetylase inhibitor comprising the cyclic tetrapeptide derivative or pharmaceutically acceptable salt thereof according to any one of claims 1 to 5 as an effective ingredient.

7. An MHC class-I molecule expression promoting agent comprising the cyclic tetrapeptide derivative or pharmaceutically acceptable salt thereof according to any one of claims 1 to 5 as an effective ingredient.

8. A pharmaceutical composition comprising the cyclic tetrapeptide derivative or pharmaceutically acceptable salt thereof according to any one of claims 1 to 5 as an effective ingredient.

9. The pharmaceutical composition according to claim 8 which is used as an anti-cancer agent.

* * * * *